(12) United States Patent
Hu et al.

(10) Patent No.: US 8,877,949 B2
(45) Date of Patent: Nov. 4, 2014

(54) FURO[3,2-G]CHROMENE COMPOUNDS AND USES THEREOF

(75) Inventors: Chun Hu, Shenyang (CN); Shihui Wang, Shenyang (CN); Yan Wang, Shenyang (CN); Erfang Huang, Shenyang (CN); Xiaoping Liu, Shenyang (CN); Dawei Li, Shenyang (CN)

(73) Assignee: Shenyang Pharmaceutical University, Shenyang (CN)

( * ) Notice: Subject to any disclaimer, the term of this patent is extended or adjusted under 35 U.S.C. 154(b) by 0 days.

(21) Appl. No.: 13/642,421

(22) PCT Filed: Apr. 13, 2011

(86) PCT No.: PCT/CN2011/000653
§ 371 (c)(1),
(2), (4) Date: Dec. 21, 2012

(87) PCT Pub. No.: WO2011/131026
PCT Pub. Date: Oct. 27, 2011

(65) Prior Publication Data
US 2013/0096112 A1 Apr. 18, 2013

(30) Foreign Application Priority Data
Apr. 20, 2010 (CN) .......................... 2010 1 0150845

(51) Int. Cl.
*C07D 493/04* (2006.01)
*A61K 31/35* (2006.01)
*A61K 31/352* (2006.01)

(52) U.S. Cl.
CPC .............. *C07D 493/04* (2013.01); *A61K 31/35* (2013.01); *A61K 31/352* (2013.01)
USPC .......................................... 549/387; 514/454

(58) Field of Classification Search
CPC .............................. C07D 493/04; A61K 31/35
USPC ............................................ 549/387; 514/454
See application file for complete search history.

(56) References Cited

U.S. PATENT DOCUMENTS 7,144,885 B2 * 12/2006 Zhang et al. ............. 514/255.05

FOREIGN PATENT DOCUMENTS

| CN | 101486713 A | 7/2009 |
| CN | 101805349 A | 8/2010 |

OTHER PUBLICATIONS

Ciana et al. (Maturitas 54 (2006) 315-320).*
Park et al. (Toxicology Lett., 120 (2001), 281-91).*
Fisher et al., "Tamoxifen for Prevention of Breast Cancer: Report of the National Surgical Adjuvant Breast and Bowel Project P-1 Study," *Journal of the National Cancer Institute* 90(18): 1371-1388, Sep. 16, 1998.
Geetanjali et al., "Linear Furano Compounds: Synthesis of 7H-Furo[3,2-g][1]benzopyran-7-ones," *Bull. Chem. Soc. Jpn. 59*: 1299-1301, 1986.
Mora et al., "Coronary Artery Disease in Postmenopausal Women," *Current Treatment Options in Cardiovascular Medicine 3*: 67-79, 2001.
Persson et al., "Risks of breast and endometrial cancer after estrogen and estrogen-progestin replacement," *Cancer Causes and Control 10*: 253-260, 1999.
Sarada et al., "Synthesis of Aroyl Benzopyrones as Possible Anti-Implantation Agents," *Indian Journal of Heterocyclic Chemistry 9*: 7-12, Jul.-Sep. 1999.
Turner et al., "Skeletal Effects of Estrogen," *Endocrine Reviews 15*(3): 275-300, 1994.
Walsh et al., "Effects of Raloxifene on Serum Lipids and Coagulation Factors in Healthy Postmenopausal Women," *JAMA 279*(18): 1445-1451, May 13, 1998.
Wang et al., "Synthesis, characterization, crystal structure and cytotoxicities of 2-aroyl-3-aryl-5H-furo[3,2-g]chromene derivatives," *ARKIVOC xi*: 204-214, Oct. 24, 2010.
Wang et al., "Design, Synthesis and Biological Evaluation of 2-Aroyl-3-aryl-6,7-dihydro-5H-furo[3,2-g]chromen Derivatives as a Novel Series of Estrogen Receptor Modulators," *Chem. Res. Chinese Universities 27*(1): 54-59, 2011.

* cited by examiner

*Primary Examiner* — Robert Havlin
(74) *Attorney, Agent, or Firm* — Seed IP Law Group PLLC

(57) ABSTRACT

Disclosed are furo[3,2-g]chromene derivatives represented by formula (I), stereoisomers, pharmaceutically acceptable salts, and pharmaceutical compositions thereof, as well as uses thereof as estrogen receptor modulators.

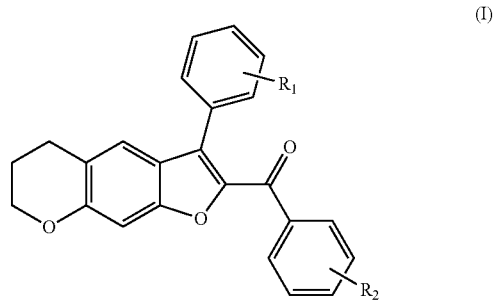

(I)

4 Claims, No Drawings

FURO[3,2-G]CHROMENE COMPOUNDS AND USES THEREOF

TECHNICAL FIELD

The invention relates to furo[3,2-g]chromene compounds, medical uses thereof as estrogen receptor modulators, and preparation methods thereof.

BACKGROUND ART

Those compounds that simulate estrogen-like actions have extensive applications for treatment and prophylaxis, including alleviating menopausal symptoms, curing acnes, treating dysmenorrheal and dysfunctional uterine bleeding, osteoporosis and prostate cancer, and preventing cardiovascular diseases.

As found by investigation, estrogen receptors are classified into two types, i.e. ERα and ERβ. Upon binding with these two subtypes, ligands exert physiological actions with different tissue specificities.

A compound that can results in a positive reaction but has no adverse side effect or reduced side effects, like an estrogen replacement therapy, is needed in the field. It is also required that this compound has an estrogen-like action on organisms with a tissue specificity. Due to their spatial structure similarity with estrogen, furochromene derivatives can simulate estrogen, bind to estrogen receptors in organisms, and thus exert physiological actions.

The compound of the invention is a ligand for an estrogen receptor. The compound can be used in treating and preventing various diseases related with the function of estrogen, including bone loss, bone fracture, osteoporosis, metastatic bone diseases, periodontal diseases, cartilage degeneration, endometriosis, uterine fibroma diseases, hot flushes, elevated LDL cholesterol level, cardiovascular diseases, cognitive function impairment, cerebrum degeneration diseases, anxiety, depression caused by insufficient estrogen, inflammation, inflammatory bowel diseases, sexual dysfunction, hypertension, retinal degeneration and cancers, particularly breast cancer, ovary cancer, osteosarcoma, endometrial carcinoma and prostate cancer.

Estrogen is a class of important hormonal compounds in human bodies. When women go into menopause, their estrogen level will drop, thereby causing climacteric syndrome, osteoporosis, senile dementia and cardiovascular system diseases etc. Regarding the dropped estrogen level during postmenopausal period, an estrogen replacement therapy (ERT) can be used, so as to significantly reduce the incidence of osteoporotic fracture and coronary heart disease during postmenopausal period (Turner R T, Riggs B L, Spelsberg T C. Endocr Rev, 1994, 15 (3): 275-300; Mora S, Kershner D W, Vigilance C P, et al. Curr Treat Options Cardiovasc Med, 2001, 3 (1): 67-79). However, ERT might induce breast cancer and endometrial carcinoma (Persson I, Weiderpass E, Bergkvist L, et al. Cancer Causes Control, 1999, 10 (4): 253-260). In order to overcome the adverse side effect of estrogen to cause cancers, a hormone replacement therapy (HRT) which involves the joint action of estrogen and progestogen has been further developed. Nevertheless, a long-term HRT might also increase the incidence of breast cancer. In other words, even though progestogen is used, the occurrence of endometrial carcinoma caused by estrogen cannot be avoided in all circumstances. Therefore, these adverse side effects limit the long-term application of HRT. Moreover, selective estrogen receptor modulators (SERMs) exert estrogen-like actions on bone and cardiovascular systems, and exhibit anti-estrogen function against uteri and breasts. However, utilization of zitazonium and raloxifene can results in some adverse side effects such as endometrial carcinoma and hot flashes, etc. (Fisher B, Costantino J P, Wickerham D L, et al. J Nati Cancer Inst, 1998, 90:1371-1388; Walsh B W, Kuller L H, Wild R A, et al. J Am Med Assoc, 1998, 279:1445-1451).

SUMMARY OF INVENTION

The technical problem solved by the invention is to provide a compound represented by formula I shown as follow, a prodrug and a pharmaceutically active metabolite thereof, as well as a stereoisomer and a pharmaceutically acceptable salt thereof. The invention also provides use of the compound for the preparation of a medicament useful for the prophylaxis and treatment of estrogen-related diseases.

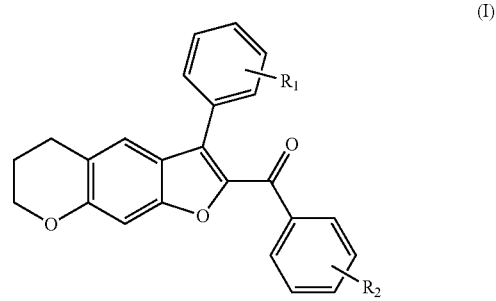

(I)

wherein
R₁ can be optionally 1, 2 or 3 groups independently selected from H, halogen, —OH, —OCH$_3$, —CH$_3$, —NO$_2$, —O(CH$_2$)$_{n_1}$NR$_3$R$_4$, —O(CH$_2$)$_{n_2}$CONR$_5$R$_6$;
R₂ can be optionally 1, 2 or 3 groups independently selected from H, halogen, —OH, —OCH$_3$, —CH$_3$, —NO$_2$, —O(CH$_2$)$_{n_1}$NR$_3$R$_4$, —O(CH$_2$)$_{n_2}$CONR$_5$R$_6$;
wherein R$_3$R$_4$ is independently selected from methyl or ethyl, or R$_3$R$_4$, together with the nitrogen atom to which they are attached, form a pyrrolidinyl, methylpyrrolidinyl, dimethylpyrrolidinyl, piperidyl, morpholinyl, or hexamethylene imine ring;
n$_1$ is an integer from 2 to 4;
R$_5$R$_6$ is independently selected from methyl or ethyl, or R$_5$R$_6$, together with the nitrogen atom to which they are attached, form a pyrrolidinyl, methylpyrrolidinyl, dimethylpyrrolidinyl, piperidyl, morpholinyl, or hexamethylene imine ring; or is independently selected from hydrogen and a substituted or unsubstituted phenyl ring group;
n$_2$ is an integer from 1 to 3.

The invention also provides a pharmaceutical composition comprising the compound represented by formula I and a pharmaceutically acceptable carrier. A pharmaceutical composition comprising a pharmaceutically acceptable carrier and any compound disclosed in the application is also contemplated in the invention. The invention also relates to a method for preparing the composition of the invention, and a method or intermediate for preparing the compound and pharmaceutical composition of the invention.

The compound of the invention can be administered by itself, or preferably in combination with a pharmaceutically acceptable carrier or diluent, and optionally, with a known adjuvant, based on the conventional pharmaceutical practice, i.e. in form of a pharmaceutical composition. The compound is administered orally or parenterally, including intravenously, intramuscularly, intraperitoneally, subcutaneously, rectally and topically.

In the tablets for oral administration, a commonly used carrier including lactose and corn starch, as well as a lubricant such as magnesium stearate are usually added. For an orally administered medicament in a form of capsule, a diluent including lactose and dry corn starch can be used. In terms of the oral routes for the therapeutic compound according to the invention, the selected compound can be administered in a form of tablet or capsule, or as an aqueous solution or suspension. As for an orally administered medicament in a form of tablet or capsule, the active pharmaceutical ingredient can be combined with an orally administered, non-toxic, pharmaceutically acceptable inert carrier, e.g. lactose, starch, sucrose, glucose, methylcellulose, magnesium stearate, dicalcium phosphate, calcium sulfate, mannitol, sorbitol and so on. As for an orally administered medicament in a form of liquid, the orally administered pharmaceutical ingredient can be combined with any orally administered, non-toxic, pharmaceutically acceptable inert carrier, e.g. ethanol, glycerol, water and so on. In addition, a suitable adhesive, lubricant, disintegrant and colorant may be added to the mixture. A suitable adhesive includes starch, gelatin, natural sugar such as glucose or lactose, a corn sweetening agent, natural and synthetic gums such as gum Arabic, gum tragacanth or sodium alginate, carboxymethylcellulose, polyethylene glycol, wax and so on. A suitable lubricant includes sodium oleate, sodium stearate, magnesium stearate, sodium benzoate, sodium acetate, sodium chloride and so on. Where an aqueous suspension is administered orally, the active ingredient can be combined with an emulsifying agent or suspension. Some sweetening agents or flavoring agents can be added as well. As for intramuscular, intraperitoneal, subcutaneous and intravenous administration, a sterile solution containing the active ingredient is usually prepared, and the pH of the solution can be adjusted and buffered appropriately. As for intravenous administration, the total concentration of the solute should be under control, so as to maintain the isotonicity of the preparation.

The compound of the invention can also be administered as a liposome administration system, e.g. in a form of small monolayer vesicle, large monolayer vesicle and multilayer vesicle. A liposome can be formed from a variety of phospholipids, e.g. cholesterol, stearylamine or phosphatidylcholine.

The compound of the invention can also be administered using a monoclonal antibody as a separate carrier, wherein the compound molecule is coupled. The compound of the invention can also be coupled with a dissoluble polymer used as the carrier of target medicament. The polymer includes polyvinylpyrrolidone, a pyran copolymer, polyhydroxypropylmethylacrylamide-phenol, polyhydroxy-ethylasparagine-phenol or palmityl-substituted polyoxyethylene-polylysine. In addition, the compound of the invention can also be coupled with a class of biodegradable polymers used for achieving controlled release of medicines. Such biodegradable polymers includes, for example, polylactic acid, polyglycolic acid, a copolymer of polylactic acid and polyglycolic acid, polycaprolactone, polyhydroxybutyric acid, polyortho esters, polyacetals, polydihydropyran, a cross-linked or amphoteric block copolymer of polycyanoacrylate and hydrogel.

The compound of the invention can also be administered in combination with a known agent useful for treating or preventing the diseases shown as follows: bone loss, osteoporosis, metastatic bone diseases, periodontal disease, cartilage degeneration, endometriosis, uterine fibroma diseases, hot flushes, elevated LDL cholesterol level, cardiovascular diseases, cognitive function impairment, cerebrum degeneration diseases, anxiety, depression caused by insufficient estrogen, inflammation, inflammatory bowel diseases, sexual dysfunction, hypertension, retinal degeneration and cancers, particularly breast cancer, uterine cancer and prostate cancer. The combinations of the compounds disclosed herein and agents useful in the treatment or prevention of the diseases disclosed herein are also within the scope of the invention. Such agents include organic diphosphonates; cathepsin K inhibitors; estrogen or estrogen receptor modulators; androgen receptor modulators; osteoclast proton ATPase inhibitors; HMG-CoA reducase inhibitors; integrin receptor antagonists; osteoblast anabolic agents e.g. PTH; calcitonin; vitamin D or synthetic vitamin D analogues; selective serotonin reuptake inhibitors (SSRIS); aromatase inhibitors; and pharmaceutically acceptable salts and mixtures thereof. A preferred combination is the combination of the compound of the invention and an organic phosphonate. Another preferred combination is the combination of the compound of the invention and a cathepsin K inhibitor. Another preferred combination is the combination of the compound of the invention and estrogen. Another preferred combination is the combination of the compound of the invention and an androgen receptor modulator. A further preferred combination is the combination of the compound of the invention and an osteoblast anabolic agent.

The term "diphosphonates" include diphosphonates and pharmaceutically acceptable salts and derivatives thereof. The term "estrogen" includes, but is not limited to naturally occurring estrogen, synthesized conjugated estrogen, oral contraceptive, and sulfated estrogen. The term "estrogen receptor modulator" means a substance used for interfering with or resisting the binding between estrogen and receptor, regardless of its mechanism. The term "cathepsin K inhibitor" means a compound capable of interfering with the activity of cysteine proteinase cathepsin K. The term "androgen receptor modulator" means a compound capable of interfering with or preventing the binding between androgen and receptor, regardless of its mechanism, including finasteride and other 5α reducase inhibitors. The term "osteoclast proton ATPase inhibitor" means an inhibitor for proton ATPase, which can be found on the epiphragm of osteoclast, and has been reported to play an important role in the process of bone reuptake. This type of proton pump represents an attracting target for the design of a bone reuptake inhibitor, and can be potentially used for treating and preventing osteoporosis and its related metabolic diseases. The term "HMG-CoA reducase inhibitor" means an inhibitor for 3-hydroxy-3-methylglutaryl-CoA reducase. A compound which has an inhibitory activity against HMG-CoA reducase can be easily identified by an assay known in the field. The term "integrin receptor antagonist" means a compound capable of selectively antagonizing, suppressing or resisting the binding between a physiological ligand and $\alpha\nu\beta3$ integrin; a compound capable of selectively antagonizing, suppressing or resisting the binding between a physiological ligand and $\alpha\nu\beta3$ integrin; a compound capable of selectively antagonizing, suppressing or resisting the binding between a physiological ligand and $\alpha\nu\beta3$ and $\alpha\nu\beta5$ integrins, or a compound capable of selectively antagonizing, suppressing or resisting the activities of specific integrins expressed by epithelial cells of capillaries. The function of antagonizing $\alpha\nu\beta3$ is selected from inhibition of bone reuptake, inhibition of restenosis, inhibition of macular degeneration, inhibition of arthritis, inhibition of cancer, and inhibition of metastasis. The term "osteoblast anabolic agent" means an agent used for bone construction, e.g. PTH.

And calcitonin can inhibit bone reuptake by suppressing the activity of osteoclast. The term "vitamin D" includes, but is not limited to vitamin D3 and vitamin D2 which are naturally existing biological inactive precursors of hydroxylated biological active metabolite of vitamin D. The term "synthetic vitamin D analogues" include artifactual compounds which have similar functions with vitamin D. The selective serotonin reuptake inhibitor acts by increasing the amount of serotonin in brain; includes, but not limited to, fluoxetine, parotine, sertraline, citalopram and fluvoxamine; and can also be used to treat estrogen-related diseases. The term "aromatase inhibitors" include compounds that inhibit aromatase, and include, but not limited to, aminoglutethimide, letrozole, formestane, exemestane, atamestane, fadrozole, fluozole, vorozole.

The term "administer" and its variations in connection with the compound of the invention (e.g. "administer" a compound) mean that the compound or a prodrug of the compound is introduced into an animal system in need of treatment. Where the inventive compound or its prodrug is provided in combination with one or more other active agents (e.g. diphosphonate compounds, etc.), the term "administer" and its variations can be interpreted to include both the simultaneous and successive introduction of the compound or its prodrug and other agents. The invention also includes the prodrugs of the inventive compounds within it extent. Usually, these prodrugs are functional derivatives of the inventive compounds, and easily converted into the desired compounds in vivo. In this way, in the treatment method of the invention, the term "administer" includes the uses of the compounds disclosed specifically or possibly, the compounds that are not disclosed specifically but can be converted into the specific compounds in the patients to whom they have been administered, so as to treat the variety of diseases. Conventional methods for selecting and preparing suitable prodrug derivatives are incorporated herein for reference. The metabolites of these compounds include the active substances generated after introducing the inventive compounds into a biological environment.

The invention also includes a pharmaceutical composition useful for the treatment of osteoporosis or other bone diseases, wherein the treatment includes administering a therapeutically effective amount of the inventive compound, and the composition comprises or does not comprise a pharmaceutically acceptable carrier or diluent. The suitable compositions of the invention include an aqueous solution containing the inventive compound and a pharmaceutically acceptable carrier, e.g. saline, with a pH higher than a certain level, e.g. pH 7.4. This solution can be introduced into the blood stream of a patient by a topical bolus.

Where the inventive compound is administered to a human subject, the daily dose, usually determined by a physician, relies on age, weight and reaction of individual patient and his/her symptomatic severity. In an exemplary application, a suitable amount of the compound is administered to a mammal in need of the treatment. In the case that the compound is used for the specified purpose, the oral dosage is about 0.01 mg/kg body weight/day (mg/kg/day)~about 100 mg/kg/day, preferably 0.01~10 mg/kg/day, most preferably 0.1~5.0 mg/kg/day in the invention. For oral administration, preferably, the composition is provided in a form of tablet containing 0.01, 0.05, 0.1, 0.5, 1.0, 2.5, 5.0, 10.0, 15.0, 25.0, 50.0, 100 and 500 mg of the active ingredient, as a dosage for adjusting the symptom of the treated patient. Generally, a medicament contains about 0.01 mg~about 500 mg of active ingredient, preferably about 1 mg~about 100 mg of active ingredient. For intravenous injection, the most preferred dosage is about 0.1~about 10 mg/kg/min during infusion at a constant rate. The compound of the invention can be administered once per day, or the total daily dose of the compound can be divided into and administered in two, three or four dosages. In addition, the preferred compound of the invention can be administered as an intranasal medicine using a suitable intranasal carrier locally, or through a transcutaneous route using a transcutaneous patch known by a person skilled in the art. For transcutaneous administration, the dosage administration is certainly consecutive rather than discrete during the entire process of administration.

The compound of the invention can be used in combination with other agents useful for treating estrogen-mediated conditions. Each component in this combination can be administered alone, or simultaneously but separately or as a single combination, in various frequencies during treatment. As a result, the invention is understood to include all these technical solutions of simultaneous or alternative treatment, so is the term "administer". Theoretically, the combination of the inventive compound and other agent useful for treating cathepsin-mediated conditions includes any combination of any pharmaceutical compositions useful for treating estrogen-related diseases.

Therefore, the invention also relates to use in combination with the second agent, wherein the second agent is selected from organic diphosphonate compounds, cathepsin K inhibitors, estrogen, estrogen receptor modulators, androgen receptor modulators, osteoclast proton ATPase inhibitors, HMG-CoA reducase inhibitors, integrin receptor antagonists, osteoblast anabolic agents, calcitonin, vitamin D, synthetic vitamin D analogues, selective serotonin reuptake inhibitors, aromatase inhibitors, and pharmaceutically acceptable salts and mixtures thereof.

The compound of the invention can be used in combination with other agents useful for treating estrogen-mediated conditions. Each component in this combination can be administered alone, or simultaneously but separately or as a single combination, in various frequencies during treatment. As a result, the invention is understood to include all these technical solutions of simultaneous or alternative treatment, so is the term "administer". Theoretically, it shall be understood that the combination of the inventive compound and other agent useful for treating estrogen-mediated conditions includes any combination of any pharmaceutical compositions useful for treating estrogen-related diseases.

The dosage regime for using the inventive compound is selected according to several factors, including the type, race, age, weight, gender and medical condition of a patient; the severity of the condition under the treatment; administration route; renal and hepatic functions of a patient; as well as the specifically used compound or salt thereof. An ordinary skilled physician, veterinarian or clinician can easily determine and prescribe an effective dosage desired for the prophylaxis, resistance or prevention of the progression of conditions.

In the method of the invention, the specifically described compound can form an active component, mixed with a suitable pharmaceutical diluent, excipient or carrier (collectively named as "carrier" substances herein) selected properly according to the administration form, i.e. oral tablets, capsules, elixirs, syrups and so on, and comply with conventional pharmaceutical practice.

The pharmaceutically acceptable salts of the inventive compounds include conventional non-toxic salts formed from inorganic or organic acids. Conventional non-toxic salts include the salts derived from inorganic acids e.g. hydrochloric acid, hydrobromic acid, sulphuric acid, sulphamic acid, phosphoric acid, and nitric acid, etc., as well as the salts prepared from organic acids, e.g. acetic acid, propionic acid, succinic acid, glycolic acid, stearic acid, lactic acid, malic acid, tartaric acid, citric acid, ascorbic acid, pamoic acid, maleic acid, hydroxymaleic acid, phenylacetic acid, glutamic acid, benzoic acid, oxybenzoic acid, sulfanilic acid, 2-acetoxy-benzoic acid, trans-butenedioic acid, toluene sulfonic acid, methylsulfonic acid, ethane-disulfonic acid, oxalic acid, isethionic acid, and trifluoroacetic acid, etc. The pharmaceutically acceptable salts of the inventive compounds can be synthesized from the inventive compounds having an acidic or alkaline portion by conventional chemical methods. Generally, salts of the alkaline compounds can be prepared by ion exchange chromatography, or by allowing the reaction between free alkali and a stoichiometric or excess amount of inorganic or organic acid desired to form the salts in a suitable solvent or various combinations of solvents. Similarly, the salts of the acidic compounds can be formed through the reaction of suitable inorganic acids or organic alkalis.

The compounds of the invention can be prepared from suitable materials according to a general process shown as follows, and are further illustrated by the following specific Examples. All known variations of the conditions and methods for the preparation below can be used to prepare these compounds as well. All temperatures used are in a unit of Celsius-degree, unless indicated otherwise.

The preparation methods in some representative Examples of the invention are shown in the flow scheme below.

Flow Scheme 1

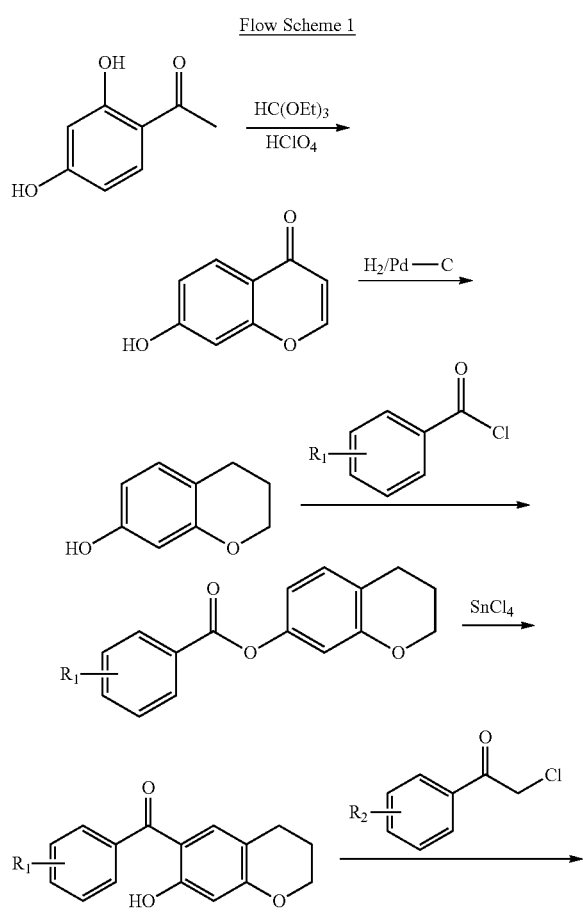

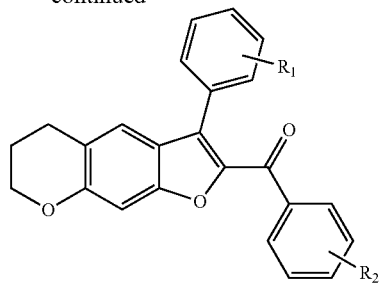

wherein
$R_1$ can be optionally 1, 2 or 3 groups independently selected from H, halogen, —OH, —OCH$_3$, —CH$_3$, —NO$_2$, —O(CH$_2$)$n_1$NR$_3$R$_4$, —O(CH$_2$)$n_2$CONR$_5$R$_6$;
$R_2$ can be optionally 1, 2 or 3 groups independently selected from H, halogen, —OH, —OCH$_3$, —CH$_3$, —NO$_2$, —O(CH$_2$)$n_1$NR$_3$R$_4$, —O(CH$_2$)$n_2$CONR$_5$R$_6$;
wherein $R_3R_4$ is independently selected from methyl or ethyl, or $R_3R_4$, together with the nitrogen atom to which they are attached, form a pyrrolidinyl, methylpyrrolidinyl, dimethylpyrrolidinyl, piperidyl, morpholinyl, or hexamethylene imine ring;
$n_1$ is an integer from 2 to 4;
$R_5R_6$ is independently selected from methyl or ethyl, or $R_5R_6$, together with the nitrogen atom to which they are attached, form a pyrrolidinyl, methylpyrrolidinyl, dimethylpyrrolidinyl, piperidyl, morpholinyl, or hexamethylene imine ring; or is independently selected from hydrogen and a substituted or unsubstituted phenyl ring group;
$n_2$ is an integer from 1 to 3.

The methods for preparing the inventive compounds are simple and have stable yields. The compounds prepared by these methods have better effects in the prevention and treatment of estrogen-related diseases.

EMBODIMENTS FOR CARRYING OUT THE INVENTION

The invention is described in detail by referring to the following Examples. However, it shall be understood that the invention is not limited to the following specifically described Examples.

Example 1

Preparation of 2-benzoyl-3-(4-methoxyphenyl)-6,7-dihydrogen-5H-furo[3,2-g]chromene To a round bottomed flask, 0.26 mol of 2',4'-dihydroxyacetophenone was added and mixed thoroughly with 232 mL of triethyl orthoformate. Then 26.4 mL of perchloric acid was dropped slowly into the resultant mixture. After 30 min reaction, 300 mL ether was added, and solids were precipitated. Following sucking filtration, the dried solids were transferred into a 1000 mL round bottomed flask, and refluxed for 2 hours after 250 mL hot water was added. Sucking filtration was conducted again, and then 22.69 g of 7-hydroxychromone was obtained by recrystallization with ethanol, with a yield of 53.2% and MS m/z (M)162.

To a 1000 mL round bottomed flask, 0.15 mol of 7-hydroxychromone, and then 2.50 g of 5% palladium carbon and 300 mL of ethanol were added. Subsequently, hydrogen was passed into the flask, and the reaction was carried out for 48 hours at 50° C. Palladium carbon was removed by sucking filtration, and ethanol was removed by rotary evaporation. Then 21.39 g of 7-hydroxychroman was obtained, with a yield of 92.4% and MS m/z (M)150.

In a 100 mL single-necked bottle, 0.1 mol of 7-hydroxychroman was dissolved in 50 mL acetone, and then 0.11 mol of triethylamine was added. Under agitation, 0.11 mol of 4-methoxybenzoyl chloride was dropped into the resultant mixture. After the reaction was completed as monitored by TLC, the reaction product was poured into 500 mL iced water, and the pH was adjusted to pH 7. Then 12.55 g of 7-(4-methoxy)-benzoyloxychroman was obtained following sucking filtration, with a yield of 90.9% and MS m/z (M)284.

Then 0.05 mol of 7-(4-methoxy)-benzoyloxychroman and 60 mL of stannic chloride were placed into a 100 mL single-opened bottle. Following reflux under heating for 12 hours, yellow solids were precipitated. After being cooled down to room temperature, the reaction solution was poured into 200 g crushed ice containing 20 mL concentrated HCl. Again, yellow solids were precipitated and sucking filtrated. Then 12.05 g of 6-(4-methoxy)benzoyl-7-hydroxychroman was obtained by recrystallization with 10 mL of absolute ethanol, with a yield of 84.9% and MS m/z (M)284. Mp: 148.4-150.5° C. $^1$H-NMR (CDCl$_3$, 600 MHz, δ: ppm): 2.00 (t, 2H, CH$_2$), 2.67 (t, 2H, CH$_2$), 3.89 (s, 3H, OCH$_3$), 4.24 (t, 2H, CH$_2$), 6.43 s, 1H, ArH), 6.99 (dd, 2H, ArH, J=8.4 Hz), 7.30 (s, 1H, ArH), 7.65 (dd, 2H, ArH, J=8.4 Hz), 12.24 (s, 1H, OH).

Subsequently, 0.005 mol of 6-(4-methoxy)benzoyl-7-hydroxychroman and 0.005 mol of bromo-acetophenone, 0.0025 mol of tetrabutyl ammonium bromide and 15 mL aqueous solution of 30% potassium carbonate, 30 mL dichloromethane were placed into a 100 mL single-opened bottle, and agitated at 30° C. for 12 h. After the reaction was completed as monitored by TLC, the organic phases were separated; the water phases were extracted with 20 mL dichloromethane; then the organic phases were combined, and washed with an aqueous solution of 2% NaOH, water, a saturated NaCl solution, respectively. Following a drying process and rotary evaporation, 0.53 g of 2-benzoyl-3-(4-methoxyphenyl)-6,7-dihydrogen-5H-furo[3,2-g]chromene was obtained by recrystallization with 10 mL of absolute ethanol, with a yield of 30.2%. Mp: 106.3-108.5° C. ESI-MS m/z (M+1) 385.13; $^1$H-NMR (600 MHz, CDCl$_3$, δ: ppm): 2.04 (t, 2H, CH$_2$), 2.91 (t, 2H, CH$_2$), 3.83 (s, 3H, OCH$_3$), 4.27 (t, 2H, CH$_2$), 6.90 (dd, 2H, ArH, J=8.4 Hz, J=1.8 Hz), 7.01 (s, 1H, ArH), 7.32 (s, 1H, ArH), 7.34-7.47 (m, 5H, ArH), 7.84 (dd, 2H, ArH, J=8.4 Hz, J=1.8 Hz).

Example 2

Preparation of 2-(4-methoxybenzoyl)-3-phenyl-6,7-dihydrogen-5H-furo[3,2-g]chromene Following the method of Example 1, 0.65 g of yellow crystal of 2-(4-methoxybenzoyl)-3-phenyl-6,7-dihydrogen-5H-furo[3,2-g]chromene was obtained, with a yield of 60% and Mp: 130.3-132.5° C. ESI-MS m/z (M+1) 385.13; $^1$HNMR (600 MHz, CDCl$_3$, δ: ppm) 2.04 (t, 2H, CH$_2$), 2.91 (t, 2H, CH$_2$), 3.83 (s, 3H, OCH$_3$), 4.26 (t, 2H, CH$_2$), 6.83 (dd, 2H, ArH, J=7.0 Hz, J=1.9 Hz), 7.03 (s, 1H, ArH), 7.30 (s, 1H, ArH), 7.35-7.49 (m, 5H, ArH), 7.90 (dd, 2H, ArH, J=7.0 Hz, J=1.9 Hz).

Example 3

Preparation of 2-(4-chlorobenzoyl)-3-(4-methoxyphenyl)-6,7-dihydrogen-5H-furo[3,2-g]chromene Following the method of Example 1, 0.56 g of yellow crystal of 2-(4-chlorobenzoyl)-3-(4-methoxyphenyl)-6,7-dihydrogen-5H-furo[3,2-g]chromene was obtained, with a yield of 60% and Mp: 135.3-137.5° C. ESI-MS m/z (M+1) 419.13; $^1$HNMR (600 MHz, CDCl$_3$, δ: ppm): 2.05 (t, 2H, CH$_2$), 2.91 (t, 2H, CH$_2$), 3.84 (s, 3H, OCH$_3$), 4.27 (t, 2H, CH$_2$), 6.92 (dd, 2H, ArH, J=7.0 Hz, J=1.9 Hz), 7.00 (s, 1H, ArH), 7.31-7.32 (m, 3H, ArH), 7.40-7.41 (m, 2H, ArH), 7.80 (dd, 2H, ArH, J=7.0 Hz, J=1.9 Hz).

Example 4

Preparation of 2-(4-methylbenzoyl)-3-(4-methoxyphenyl)-6,7-dihydrogen-5H-furo[3,2-g]chromene Following the method of Example 1, 0.69 g of 2-(4-methylbenzoyl)-3-(4-methoxyphenyl)-6,7-dihydrogen-5H-furo[3,2-g]chromene was obtained, with a yield of 60% and ESI-MS m/z (M+1) 399.13; $^1$HNMR (600 MHz, CDCl$_3$, δ: ppm): 2.05 (t, 2H, CH$_2$), 2.34 (s, 3H, CH$_3$), 2.91 (t, 2H, CH$_2$), 3.84 (s, 3H, OCH$_3$), 4.27 (t, 2H, CH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 5

Preparation of 2-(4-methoxybenzoyl)-3-(4-methoxyphenyl)-6,7-dihydrogen-5H-furo[3,2-g]chromene Following the method of Example 1, 0.75 g of 2-(4-methoxybenzoyl)-3-(4-methoxyphenyl)-6,7-dihydrogen-5H-furo[3,2-g]chromene was obtained, with a yield of 60% and ESI-MS m/z (M+1) 415.13; $^1$HNMR (600 MHz, CDCl$_3$, δ: ppm): 2.05 (t, 2H, CH$_2$), 2.91 (t, 2H, CH$_2$), 3.84 (s, 6H, OCH$_3$), 4.27 (t, 2H, CH$_2$), 7.05 (dd, 2H, ArH, J=7.0 Hz, J=1.9 Hz), 7.18 (dd, 2H, ArH, J=7.0 Hz, J=1.9 Hz), 7.47 (s, 1H, ArH), 7.55 (s, 1H, ArH), 7.68 (dd, 2H, ArH, J=7.0 Hz, J=1.9 Hz), 7.78 (dd, 2H, ArH, J=7.0 Hz, J=1.9 Hz).

Example 6

Preparation of 2-(4-hydroxybenzoyl)-3-phenyl-6,7-dihydrogen-5H-furo[3,2-g]chromene Under agitation at −15° C., a dichloromethane solution containing 1 mmol of boron tribromide was added to a dichloromethane solution containing 1 mmol of 2-(4-methoxybenzoyl)-3-phenyl-6,7-dihydrogen-5H-furo[3,2-g]chromene accordingly, and then reacted for 4 h. The progress of the reaction was traced by TLC. After the reaction was completed, the reaction product was poured into 50 mL water. Following sucking filtration, 0.24 g of desired product was obtained by recrystallization with ethanol, with a yield of 80% and ESI-MS m/z (M+1) 371.13; $^1$HNMR (600 MHz, CDCl$_3$, δ: ppm): 2.05 (t, 2H, CH$_2$), 2.91 (t, 2H, CH$_2$), 4.27 (t, 2H, CH$_2$), 6.89 (dd, 2H, ArH, J=7.0 Hz, J=1.9 Hz), 7.41-7.55 (m, 7H, ArH), 7.72 (dd, 2H, ArH, J=7.0 Hz, J=1.9 Hz).

Example 7

Preparation of 2-benzoyl-3-(4-hydroxyphenyl)-6,7-dihydrogen-5H-furo[3,2-g]chromene Following the method of Example 6, 0.75 g of 2-benzoyl-3-(4-hydroxyphenyl)-6,7-dihydrogen-5H-furo[3,2-g]chromene was obtained, with a yield of 80% and ESI-MS m/z (M+1) 371.13; $^1$HNMR (600 MHz, CDCl$_3$, δ: ppm): 2.05 (t, 2H, CH$_2$), 2.91 (t, 2H, CH$_2$), 4.27 (t, 2H, CH$_2$), 6.86 (dd, 2H, ArH, J=7.0 Hz, J=1.9 Hz), 7.47 (s, 1H, ArH), 7.55 (s, 1H, ArH), 7.63-7.73 (m, 5H, ArH), 7.89 (dd, 2H, ArH, J=7.0 Hz, J=1.9 Hz).

Example 8

Preparation of 2-(4-chlorobenzoyl)-3-(4-hydroxyphenyl)-6,7-dihydrogen-5H-furo[3,2-q]chromene Following the method of Example 6, 0.75 g of 2-(4-chlorobenzoyl)-3-(4-hydroxyphenyl)-6,7-dihydrogen-5H-furo[3,2-g]chromene was obtained with a yield of 60% and ESI-MS m/z (M+1) 405.08; $^1$HNMR (600 MHz, CDCl$_3$, δ: ppm): 2.05 (t, 2H, CH$_2$), 2.91 (t, 2H, CH$_2$), 4.27 (t, 2H, CH$_2$), 6.86 (dd, 2H, ArH, J=7.0 Hz, J=1.9 Hz), 7.47 (s, 1H, ArH), 7.55 (s, 1H, ArH), 7.62-7.68 (m, 4H, ArH), 7.94 (dd, 2H, ArH, J=7.0 Hz, J=1.9 Hz).

Example 9

Preparation of 2-(4-methylbenzoyl)-3-(4-hydroxyphenyl)-6,7-dihydrogen-5H-furo[3,2-g]chromene Following the method of Example 6, 0.75 g of 2-(4-methylbenzoyl)-3-(4-hydroxyphenyl)-6,7-dihydrogen-5H-furo[3,2-g]chromene was obtained, with a yield of 60% and ESI-MS m/z (M+1) 385.08; $^1$HNMR (600 MHz, CDCl$_3$, δ: ppm): 2.05 (t, 2H, CH$_2$), 2.34 (s, 3H, CH$_3$), 2.91 (t, 2H, CH$_2$), 4.27 (t, 2H, CH$_2$), 6.86 (dd, 2H, ArH, J=7.0 Hz, J=1.9 Hz), 7.42-7.47 (m, 3H, ArH), 7.55 (s, 1H, ArH), 7.62 (dd, 2H, ArH, J=7.0 Hz, J=1.9 Hz), 7.77 (dd, 2H, ArH, J=7.0 Hz, J=1.9 Hz).

Example 10

Preparation of 2-(4-bromobenzoyl)-3-(4-hydroxyphenyl)-6,7-dihydrogen-5H-furo[3,2-g]chromene Following the method of Example 6, 0.75 g of 2-(4-bromobenzoyl)-3-(4-hydroxyphenyl)-6,7-dihydrogen-5H-furo[3,2-g]chromene was obtained, with a yield of 60% and ESI-MS m/z (M+1) 449.08; $^1$HNMR (600 MHz, CDCl$_3$, δ: ppm): 2.05 (t, 2H, CH$_2$), 2.91 (t, 2H, CH$_2$), 4.27 (t, 2H, CH$_2$), 6.86 (dd, 2H, ArH, J=7.0 Hz, J=1.9 Hz), 7.47 (s, 1H, ArH), 7.55 (s, 1H, ArH), 7.62-7.65 (m, 4H, ArH), 7.79 (dd, 2H, ArH, J=7.0 Hz, J=1.9 Hz).

Example 11

Preparation of 2-(4-hydroxybenzoyl)-3-(4-methoxyphenyl)-6,7-dihydrogen-5H-furo[3,2-g]chromene Following the method of Example 6, 0.67 g of 2-(4-hydroxybenzoyl)-3-(4-methoxyphenyl)-6,7-dihydrogen-5H-furo[3,2-g]chromene was obtained, with a yield of 60% and ESI-MS m/z (M+1) 401.08; $^1$HNMR (600 MHz, CDCl$_3$, δ: ppm): 2.05 (t, 2H, CH$_2$), 2.91 (t, 2H, CH$_2$), 3.83 (s, 3H, OCH$_3$), 4.27 (t, 2H, CH$_2$), 6.89 (dd, 2H, ArH, J=7.0 Hz, J=1.9 Hz), 7.05 (dd, 2H, ArH, J=7.0 Hz, J=1.9 Hz), 7.47 (s, 1H, ArH), 7.55 (s, 1H, ArH), 7.68-7.72 (m, 4H, ArH).

Example 12

Preparation of 2-(4-hydroxybenzoyl)-3-(4-hydroxyphenyl)-6,7-dihydrogen-5H-furo[3,2-g]chromene Following the method of Example 6, 0.60 g of 2-(4-hydroxybenzoyl)-3-(4-hydroxyphenyl)-6,7-dihydrogen-5H-furo[3,2-g]chromene was obtained, with a yield of 60% and ESI-MS m/z (M+1) 387.12; $^1$HNMR (600 MHz, CDCl$_3$, δ: ppm): 2.05 (t, 2H, CH$_2$), 2.91 (t, 2H, CH$_2$), 4.27 (t, 2H, CH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Example 13

Preparation of 2-[4-(morpholinoethoxy)benzoyl]-3-phenyl-6,7-dihydrogen-5H-furo[3,2-g]chromene Under agitation at room temperature, to an acetone or ethanol solution containing 1 mmol of 2-(4-hydroxybenzoyl)-3-phenyl-6,7-dihydrogen-5H-furo[3,2-g]chromene, 1 mmol of chloroethylmorpholine hydrochloride was added accordingly. Then after 1 mmol of deacid reagent (anhydrous potassium carbonate or triethylamine) and 0.1 mmol of potassium iodide catalyst were added to the resultant mixture, reflux reaction was carried out, and the progress of the reaction was traced by TLC. After the reaction was completed, the reaction solution was cooled down to room temperature and then concentrated to dryness. Sequentially 30 mL saturated saline was added, and extraction was conducted with ether. The organic layer was dried and concentrated, so as to obtain a crude product. Following recrystallization with ethanol, 0.24 g desired product was obtained with a yield of 50% and ESI-MS m/z (M+1) 484.22; $^1$HNMR (600 MHz, CDCl$_3$, δ: ppm): 2.05 (t, 2H, CH$_2$), 2.91 (t, 2H, CH$_2$), 3.06 (t, 2H, NCH$_2$), 3.44 (s, 2H, NCH$_2$), 3.55 (m, 2H, NCH$_2$), 4.01 (m, 2H, OCH$_2$), 4.26-4.32 (m, 4H, OCH$_2$), 4.64 (s, 2H, OCH$_2$), 6.84 (dd, 2H, ArH, J=7.0 Hz, J=1.9 Hz), 7.02 (s, 1H, ArH), 7.30 (s, 1H, ArH), 7.36-7.41 (m, 3H, ArH), 7.48 (m, 2H, ArH), 7.91 (dd, 2H, ArH, J=7.0 Hz, J=1.9 Hz).

Example 14

Preparation of 2-[4-(piperidinoethoxy)benzoyl]-3-phenyl-6,7-dihydrogen-5H-furo[3,2-g]chromene Following the method of Example 13, 0.23 g of 2-[4-(piperidinoethoxy)benzoyl]-3-phenyl-6,7-dihydrogen-5H-furo[3,2-g]chromene was obtained, with a yield of 51% and ESI-MS m/z (M+1) 482.25; $^1$HNMR (600 MHz, CDCl$_3$, δ: ppm): 1.45 (s, 2H, CH$_2$), 1.59-1.63 (m, 4H, CH$_2$), 2.05 (t, 2H, CH$_2$), 2.50 (s, 4H, NCH$_2$), 2.77 (t, 2H, NCH$_2$), 2.90 (t, 2H, CH$_2$), 4.13 (t, 2H, OCH$_2$), 4.26 (t, 2H, OCH$_2$), 6.82 (dd, 2H, ArH, J=7.0 Hz, J=1.9 Hz), 7.02 (s, 1H, ArH), 7.30 (s, 1H, ArH), 7.33-7.38 (m, 3H, ArH), 7.47 (m, 2H, ArH), 7.87 (dd, 2H, ArH, J=7.0 Hz, J=1.9 Hz).

Example 15

Preparation of 2-[4-(morpholine-2-oxo-ethoxy)benzoyl]-3-phenyl-6,7-dihydrogen-5H-furo[3,2-g]chromene Following the method of Example 13, 0.23 g of 2-[4-(morpholine-2-oxo-ethoxy)benzoyl]-3-phenyl-6,7-dihydrogen-5H-furo[3,2-g]chromene was obtained, with a yield of 51% and ESI-MS m/z (M+1) 498.18; $^1$HNMR (600 MHz, CDCl$_3$, δ: ppm): 2.05 (t, 2H, CH$_2$), 2.91 (t, 2H, CH$_2$), 3.61 (m, 2H, NCH$_2$), 3.66-3.72 (m, 6H), 4.27 (t, 2H, OCH$_2$), 4.69 (s, 2H, OCH$_2$), 6.95 (dd, 2H, ArH, J=7.0 Hz, J=1.9 Hz), 7.01 (s, 1H, ArH), 7.30 (s, 1H, ArH), 7.35 (m, 2H, ArH), 7.43-7.48 (m, 3H, ArH), 7.85 (dd, 2H, ArH, J=7.0 Hz, J=1.9 Hz).

Example 16

Preparation of 2-[4-(piperidine-2-oxo-ethoxy)benzoyl]-3-phenyl-6,7-dihydrogen-5H-furo[3,2-g]chromene Following the method of Example 13, 0.23 g of 2-[4-(piperidine-2-oxoethoxy)benzoyl]-3-phenyl-6,7-dihydrogen-5H-furo[3,2-g]chromene was obtained, with a yield of 51% and ESI-MS m/z (M+1) 496.18; $^1$HNMR (600 MHz, CDCl$_3$, δ: ppm): 1.58-1.68 (m, 6H), 2.05 (t, 2H, CH$_2$), 2.91 (t, 2H, CH$_2$), 3.49 (m, 2H, NCH$_2$), 3.59 (m, 2H, NCH$_2$), 4.27 (t, 2H, OCH$_2$), 4.69 (s, 2H, OCH$_2$), 6.95 (dd, 2H, ArH, J=9.0 Hz, J=3.0 Hz), 7.01 (s, 1H, ArH), 7.31 (s, 1H, ArH), 7.34 (m, 2H, ArH), 7.41-7.47 (m, 3H, ArH), 7.83 (dd, 2H, ArH, J=9.0 Hz, J=3.0 Hz).

Example 17

Preparation of 2-[4-(diethylamino-2-oxo-ethoxy)benzoyl]-3-phenyl-6,7-dihydrogen-5H-furo[3,2-g]chromene Following the method of Example 13, 0.23 g of 2-[4-(diethylamino-2-oxo-ethoxy)benzoyl]-3-phenyl-6,7-dihydrogen-5H-furo[3,2-g]chromene was obtained, with a yield of 51% and ESI-MS m/z (M+1) 484.22; $^1$HNMR (600 MHz, CDCl$_3$, δ: ppm): 1.17 (t, 3H, CH$_3$), 1.24 (t, 3H, CH$_3$), 2.05 (t, 2H, CH$_2$), 2.91 (t, 2H, CH$_2$), 3.38-3.44 (m, 4H, NCH$_2$), 4.27 (t, 2H, OCH$_2$), 4.68 (s, 2H, OCH$_2$), 6.94 (dd, 2H, ArH, J=9.0 Hz, J=3.0 Hz), 7.01 (s, 1H, ArH), 7.31 (s, 1H, ArH), 7.34 (m, 2H, ArH), 7.40-7.46 (m, 3H, ArH), 7.82 (dd, 2H, ArH, J=9.0 Hz, J=3.0 Hz).

Example 18

Preparation of 2-[4-(dimethylamino-2-oxo-ethoxy)benzoyl]-3-phenyl-6,7-dihydrogen-5H-furo[3,2-g]chromene Following the method of Example 13, 0.23 g of 2-[4-(dimethylamino-2-oxo-ethoxy)benzoyl]-3-phenyl-6,7-dihydrogen-5H-furo[3,2-g]chromene was obtained, with a yield of 51% and ESI-MS m/z (M+1) 456.17; $^1$HNMR (600 MHz, CDCl$_3$, δ: ppm): 2.05 (t, 2H, CH$_2$), 2.91 (t, 2H, CH$_2$), 3.50 (m, 6H, NCH$_3$), 4.27 (t, 2H, OCH$_2$), 4.68 (s, 2H, OCH$_2$), 6.94 (dd, 2H, ArH, J=9.0 Hz, J=3.0 Hz), 7.01 (s, 1H, ArH), 7.31 (s, 1H, ArH), 7.34 (m, 2H, ArH), 7.40-7.46 (m, 3H, ArH), 7.82 (dd, 2H, ArH, J=9.0 Hz, J=3.0 Hz).

Example 19

Preparation of 2-benzoyl-3-[4-(morpholinoethoxy)phenyl]-6,7-dihydrogen-5H-furo[3,2-g]chromene Following the method of Example 13, 0.24 g of 2-benzoyl-3-[4-(morpholinoethoxy)phenyl]-6,7-dihydrogen-5H-furo[3,2-g]chromene was obtained, with a yield of 50% and ESI-MS m/z (M+1) 484.22; $^1$HNMR (600 MHz, CDCl$_3$, δ: ppm): 2.05 (t, 2H, CH$_2$), 2.91 (t, 2H, CH$_2$), 3.06 (t, 2H, NCH$_2$), 3.44 (s, 2H, NCH$_2$), 3.55 (m, 2H, NCH$_2$), 4.01 (m, 2H, OCH$_2$), 4.26-4.32 (m, 4H, OCH$_2$), 4.64 (s, 2H, OCH$_2$), 6.84 (dd, 2H, ArH, J=7.0 Hz, J=1.9 Hz), 7.02 (s, 1H, ArH), 7.30 (s, 1H, ArH), 7.36-7.41 (m, 3H, ArH), 7.48 (m, 2H, ArH), 7.91 (dd, 2H, ArH, J=7.0 Hz, J=1.9 Hz).

Example 20

Preparation of 2-benzoyl-3-[4-(piperidinoethoxy)phenyl]-6,7-dihydrogen-5H-furo[3,2-g]chromene Following the method of Example 13, 0.24 g of 2-benzoyl-3-[4-(piperidinoethoxy)phenyl]-6,7-dihydrogen-5H-furo[3,2-g]chromene was obtained, with a yield of 50% and ESI-MS m/z (M+1) 482.25; $^1$HNMR (600 MHz, CDCl$_3$, δ: ppm): 1.45 (m, 2H, CH$_2$), 1.59-1.63 (m, 4H, CH$_2$), 2.05 (t, 2H, CH$_2$), 2.50 (s, 4H, NCH$_2$), 2.77 (t, 2H, NCH$_2$), 2.90 (t, 2H, CH$_2$), 4.13 (t, 2H, OCH$_2$), 4.26 (t, 2H, OCH$_2$), 6.82 (dd, 2H, ArH, J=7.0 Hz, J=1.9 Hz), 7.02 (s, 1H, ArH), 7.30 (s, 1H, ArH), 7.33-7.38 (m, 3H, ArH), 7.47 (m, 2H, ArH), 7.87 (dd, 2H, ArH, J=7.0 Hz, J=1.9 Hz).

Example 21

Preparation of 2-benzoyl-3-[4-(diethylaminoethoxy)phenyl]-6,7-dihydrogen-5H-furo[3,2-g]chromene Following the method of Example 13, 0.24 g of 2-benzoyl-3-[4-(diethylaminoethoxy)phenyl]-6,7-dihydrogen-5H-furo[3,2-g]chromene was obtained, with a yield of 50% and ESI-MS m/z (M+1) 470.25; $^1$HNMR (600 MHz, CDCl$_3$, δ: ppm): 1.48 (t, 6H, CH$_3$), 2.05 (t, 2H, CH$_2$), 2.90 (t, 2H, CH$_2$), 3.24-3.30 (m, 4H, NCH$_2$), 3.47 (s, 2H, NCH$_2$), 4.27 (t, 2H, OCH$_2$), 4.59 (s, 2H, OCH$_2$), 6.92 (dd, 2H, ArH, J=7.0 Hz, J=1.9 Hz), 7.02 (s, 1H, ArH), 7.29 (s, 1H, ArH), 7.36-7.39 (m, 2H, ArH), 7.46-7.51 (m, 3H, ArH), 7.88 (dd, 2H, ArH, J=7.0 Hz, J=1.9 Hz).

Example 22

Preparation of 2-[4-(diethylaminoethoxy)benzoyl]-3-phenyl-6,7-dihydrogen-5H-furo[3,2-g]chromene Following the method of Example 13, 0.24 g of 2-[4-(diethylaminoethoxy)benzoyl]-3-phenyl-6,7-dihydrogen-5H-furo[3,2-g]chromene was obtained, with a yield of 50% and ESI-MS m/z (M+1) 470.25; $^1$HNMR (600 MHz, CDCl$_3$, δ: ppm): 1.48 (t, 6H, CH$_3$), 2.05 (t, 2H, CH$_2$), 2.90 (t, 2H, CH$_2$), 3.24-3.33 (m, 4H, NCH$_2$), 3.48 (s, 2H, NCH$_2$), 4.27 (t, 2H, OCH$_2$), 4.60 (s, 2H, OCH$_2$), 6.84 (s, 2H, ArH), 7.02 (s, 1H, ArH), 7.30 (s, 1H, ArH), 7.37-7.39 (m, 3H, ArH), 7.46-7.51 (m, 2H, ArH), 7.89 (s, 2H, ArH).

Example 23

Preparation of 2-benzoyl-3-[4-(morpholine-2-oxo-ethoxy)phenyl]-6,7-dihydrogen-5H-furo[3,2-g]chromene Following the method of Example 13, 0.24 g of 2-benzoyl-3-[4-(morpholine-2-oxo-ethoxy)phenyl]-6,7-dihydrogen-5H-furo[3,2-g]chromene was obtained, with a yield of 50% and ESI-MS m/z (M+1) 498.18; $^1$HNMR (600 MHz, CDCl$_3$, δ: ppm): 2.05 (t, 2H, CH$_2$), 2.90 (t, 2H, CH$_2$), 3.60-3.72 (m, 8H), 4.27 (t, 2H, OCH$_2$), 4.71 (s, 2H, OCH$_2$), 6.95 (dd, 2H, ArH, J=8.4 Hz, J=2.4 Hz), 7.01 (s, 1H, ArH), 7.30 (s, 1H, ArH), 7.33-7.36 (m, 2H, ArH), 7.43-7.48 (m, 3H, ArH), 7.85 (dd, 2H, ArH, J=8.4 Hz, J=2.4 Hz).

Example 24

Preparation of 2-benzoyl-3-[4-(piperidine-2-oxo-ethoxy)phenyl]-6,7-dihydrogen-5H-furo[3,2-g]chromene Following the method of Example 13, 0.24 g of 2-benzoyl-3-[4-(piperidine-2-oxo-ethoxy)phenyl]-6,7-dihydrogen-5H-furo[3,2-g]chromene was obtained, with a yield of 50% and ESI-MS m/z (M+1) 496.2; $^1$HNMR (600 MHz, CDCl$_3$, δ: ppm): 1.58-1.68 (m, 6H), 2.05 (t, 2H, CH2), 2.91 (t, 2H, CH2), 3.49 (m, 2H, NCH2), 3.59 (m, 2H, NCH2), 4.27 (t, 2H, OCH2), 4.69 (s, 2H, OCH2), 6.95 (dd, 2H, ArH, J=9.0 Hz, J=3.0 Hz), 7.01 (s, 1H, ArH), 7.31 (s, 1H, ArH), 7.34 (m, 2H, ArH), 7.41-7.47 (m, 3H, ArH), 7.83 (dd, 2H, ArH, J=9.0 Hz, J=3.0 Hz).

Example 25

Preparation of 2-benzoyl-3-[4-(diethylamino-2-oxo-ethoxy)phenyl]-6,7-dihydrogen-5H-furo[3,2-g]chromene Following the method of Example 13, 0.24 g of 2-benzoyl-3-[4-(diethylamino-2-oxo-ethoxy)phenyl]-6,7-dihydrogen-5H-furo[3,2-g]chromene was obtained, with a yield of 50% and ESI-MS m/z (M+1) 484.22; $^1$HNMR (600 MHz, CDCl3, δ: ppm): 1.17 (t, 3H, CH3), 1.24 (t, 3H, CH3), 2.05 (t, 2H, CH2), 2.91 (t, 2H, CH2), 3.38-3.44 (m, 4H, NCH2), 4.27 (t, 2H, OCH2), 4.68 (s, 2H, OCH2), 6.95 (dd, 2H, ArH, J=9.0 Hz, J=3.0 Hz), 7.01 (s, 1H, ArH), 7.31 (s, 1H, ArH), 7.34 (m, 2H, ArH), 7.40-7.46 (m, 3H, ArH), 7.82 (dd, 2H, ArH, J=9.0 Hz, J=3.0 Hz).

Example 26

Preparation of 2-benzoyl-3-[4-(dimethylamino-2-oxo-ethoxy)phenyl]-6,7-dihydrogen-5H-furo[3,2-g]chromene Following the method of Example 13, 0.24 g of 2-benzoyl-3-[4-(dimethylamino-2-oxo-ethoxy)phenyl]-6,7-dihydrogen-5H-furo[3,2-g]chromene was obtained, with a yield of 50% and ESI-MS m/z (M+1) 456.17; $^1$HNMR (600 MHz, CDCl$_3$, δ: ppm): 2.05 (t, 2H, CH$_2$), 2.91 (t, 2H, CH$_2$), 3.01 (s, 3H, NCH$_3$), 3.11 (s, 3H, NCH$_3$), 4.27 (t, 2H, OCH$_2$), 4.71 (s, 2H, OCH$_2$), 6.95 (dd, 2H, ArH, J=9.0 Hz, J=3.0 Hz), 7.01 (s, 1H, ArH), 7.31 (s, 1H, ArH), 7.34 (m, 2H, ArH), 7.41-7.47 (m, 3H, ArH), 7.84 (dd, 2H, ArH, J=9.0 Hz, J=3.0 Hz).

Example 27

Preparation of 2-benzoyl-3-[4-(anilino-2-oxo-ethoxy)phenyl]-6,7-dihydrogen-5H-furo[3,2-g]chromene Following the method of Example 13, 0.24 g of 2-benzoyl-3-[4-(anilino-2-oxo-ethoxy)phenyl]-6,7-dihydrogen-5H-furo[3,2-g]chromene was obtained, with a yield of 50% and ESI-MS m/z (M+1) 504.17; $^1$HNMR (600 MHz, CDCl$_3$, δ: ppm): 2.05 (t, 2H, CH$_2$), 2.91 (t, 2H, CH$_2$), 4.27 (t, 2H, OCH$_2$), 4.65 (s, 2H, OCH$_2$), 7.00-7.02 (m, 3H, ArH), 7.18 (t, 1H, ArH), 7.30 (s, 1H, ArH), 7.33-7.50 (m, 7H, ArH), 7.61 (dd, 2H, ArH, J=9.0 Hz, J=3.0 Hz), 7.86 (dd, 2H, ArH, J=8.4 Hz, J=2.4 Hz), 8.25 (s, 1H, NH).

Example 28

Preparation of 2-benzoyl-3-[4-(benzylamino-2-oxo-ethoxy)phenyl]-6,7-dihydrogen-5H-furo[3,2-g]chromene Following the method of Example 13, 0.24 g of 2-benzoyl-3-[4-(benzylamino-2-oxo-ethoxy)phenyl]-6,7-dihydrogen-5H-furo[3,2-g]chromene was obtained, with a yield of 50% and ESI-MS m/z (M+1) 518.19; $^1$HNMR (600 MHz, CDCl$_3$, δ: ppm): 2.05 (t, 2H, CH$_2$), 2.91 (t, 2H, CH$_2$), 4.27 (t, 2H, OCH$_2$), 4.58 (m, 4H, CH$_2$), 6.92 (dd, 2H, ArH, J=8.4 Hz, J=2.4 Hz), 7.01 (s, 1H, ArH), 7.30 (s, 1H, ArH), 7.31-7.38 (m, 7H, ArH), 7.47 (m, 3H, ArH), 7.86 (dd, 2H, ArH, J=8.4 Hz, J=2.4 Hz).

Example 29

Preparation of 2-(4-chlorobenzoyl)-3-[4-(morpholinoethoxy)phenyl]-6,7-dihydrogen-5H-furo[3,2-g]chromene Following the method of Example 13, 0.24 g of 2-(4-chlorobenzoyl)-3-[4-(morpholinoethoxy)phenyl]-6,7-dihydrogen-5H-furo[3,2-g]chromene was obtained, with a yield of 50% and ESI-MS m/z (M+1) 518.17; $^1$HNMR (600 MHz, CDCl$_3$, δ: ppm): 2.05 (t, 2H, CH$_2$), 2.91 (t, 2H, CH$_2$), 3.06 (t, 2H, NCH$_2$), 3.44 (s, 2H, NCH$_2$), 3.55 (m, 2H, NCH$_2$), 4.01 (m, 2H, OCH$_2$), 4.26-4.32 (m, 4H, OCH$_2$), 4.64 (s, 2H, OCH$_2$), 6.92 (dd, 2H, ArH, J=7.0 Hz, J=1.9 Hz), 7.00 (s, 1H, ArH), 7.31-7.32 (m, 3H, ArH), 7.40-7.41 (m, 2H, ArH), 7.80 (dd, 2H, ArH, J=7.0 Hz, J=1.9 Hz).

Example 30

Preparation of 2-(4-chlorobenzoyl)-3-[4-(piperidinoethoxy)phenyl]-6,7-dihydrogen-5H-furo[3,2-g]chromene Following the method of Example 13, 0.24 g of 2-(4-chlorobenzoyl)-3-[4-(piperidinoethoxy)phenyl]-6,7-dihydrogen-5H-furo[3,2-g]chromene was obtained, with a yield of 50% and ESI-MS m/z (M+1) 516.19; $^1$HNMR (600 MHz, CDCl$_3$, δ: ppm): 1.45 (m, 2H, CH$_2$), 1.59-1.63 (m, 4H, CH$_2$), 2.05 (t, 2H, CH$_2$), 2.50 (s, 4H, NCH$_2$), 2.77 (t, 2H, NCH$_2$), 2.90 (t, 2H, CH$_2$), 4.13 (t, 2H, OCH$_2$), 4.26 (t, 2H, OCH$_2$), 6.92 (dd, 2H, ArH, J=7.0 Hz, J=1.9 Hz), 7.00 (s, 1H, ArH), 7.31-7.32 (m, 3H, ArH), 7.40-7.41 (m, 2H, ArH), 7.80 (dd, 2H, ArH, J=7.0 Hz, J=1.9 Hz).

Example 31

Preparation of 2-(4-chlorobenzoyl)-3-[4-(diethylaminoethoxy)phenyl]-6,7-dihydrogen-5H-furo[3,2-g]chromene Following the method of Example 13, 0.24 g of 2-(4-chlorobenzoyl)-3[4-(diethylaminoethoxy)phenyl]-6,7-dihydrogen-5H-furo[3,2-g]chromene was obtained, with a yield of 50% and ESI-MS m/z (M+1) 504.19; $^1$HNMR (600 MHz, CDCl$_3$, δ: ppm): 1.48 (t, 6H, CH$_3$), 2.05 (t, 2H, CH$_2$), 2.90 (t, 2H, CH$_2$), 3.24-3.33 (m, 4H, NCH$_2$), 3.48 (s, 2H, NCH$_2$), 4.27 (t, 2H, OCH$_2$), 4.60 (s, 2H, OCH$_2$), 6.92 (dd, 2H, ArH, J=7.0 Hz, J=1.9 Hz), 7.00 (s, 1H, ArH), 7.31-7.32 (m, 3H, ArH), 7.40-7.41 (m, 2H, ArH), 7.80 (dd, 2H, ArH, J=7.0 Hz, J=1.9 Hz).

Example 32

Preparation of 2-(4-chlorobenzoyl)-3-[4-(dimethylaminoethoxy)phenyl]-6,7-dihydrogen-5H-furo[3,2-g]chromene Following the method of Example 13, 0.24 g of 2-(4-chlorobenzoyl)-3-[4-(dimethylaminoethoxy)phenyl]-6,7-dihydrogen-5H-furo[3,2-g]chromene was obtained, with a yield of 50% and ESI-MS m/z (M+1) 476.16; $^1$HNMR (600 MHz, CDCl$_3$, δ: ppm): 2.05 (t, 2H, CH$_2$), 2.90 (t, 2H, CH$_2$), 3.05 (s, 6H, NCH$_3$), 3.15 (t, 2H, NCH$_2$), 4.27 (t, 2H, OCH$_2$), 4.60 (s, 2H, OCH$_2$), 6.92 (dd, 2H, ArH, J=7.0 Hz, J=1.9 Hz), 7.00 (s, 1H, ArH), 7.31-7.32 (m, 3H, ArH), 7.40-7.41 (m, 2H, ArH), 7.80 (dd, 2H, ArH, J=7.0 Hz, J=1.9 Hz).

Example 33

Preparation of 2-(4-methylbenzoyl)-3-[4-(morpholinoethoxy)phenyl]-6,7-dihydrogen-5H-furo[3,2-g]chromene Following the method of Example 13, 0.24 g of 2-(4-methylbenzoyl)-3-[4-(morpholinoethoxy)phenyl]-6,7-dihydrogen-5H-furo[3,2-g]chromene was obtained, with a yield of 50% and ESI-MS m/z (M+1) 498.22; $^1$HNMR (600 MHz, CDCl$_3$, δ: ppm): 2.05 (t, 2H, CH$_2$), 2.91 (t, 2H, CH$_2$), 3.06 (t, 2H, NCH$_2$), 3.44 (s, 2H, NCH$_2$), 3.55 (m, 2H, NCH$_2$), 4.01 (m, 2H, OCH$_2$), 4.26-4.32 (m, 4H, OCH$_2$), 4.64 (s, 2H, OCH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 34

Preparation of 2-(4-methylbenzoyl)-3-[4-(piperidinoethoxy)phenyl]-6,7-dihydrogen-5H-furo[3,2-g]chromene Following the method of Example 13, 0.24 g of 2-(4-methylbenzoyl)-3-[4-(piperidinoethoxy)phenyl]-6,7-dihydrogen-5H-furo[3,2-g]chromene was obtained, with a yield of 50% and ESI-MS m/z (M+1) 496.24; $^1$HNMR (600 MHz, CDCl$_3$, δ: ppm): 1.45 (m, 2H, CH$_2$), 1.59-1.63 (m, 4H, CH$_2$), 2.05 (t, 2H, CH$_2$), 2.50 (s, 4H, NCH$_2$), 2.77 (t, 2H, NCH$_2$), 2.90 (t, 2H, CH$_2$), 4.13 (t, 2H, OCH$_2$), 4.26 (t, 2H, OCH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 35

Preparation of 2-(4-methylbenzoyl)-3-[4-(diethylaminoethoxy)phenyl]-6,7-dihydrogen-5H-furo[3,2-g]chromene Following the method of Example 13, 0.24 g of 2-(4-methylbenzoyl)-3-[4-(diethylaminoethoxy)phenyl]-6,7-dihydrogen-5H-furo[3,2-g]chromene was obtained, with a yield of 50% and ESI-MS m/z (M+1) 484.24; $^1$HNMR (600 MHz, CDCl$_3$, δ: ppm): 1.48 (t, 6H, CH$_3$), 2.05 (t, 2H, CH$_2$), 2.90 (t, 2H, CH$_2$), 3.24-3.33 (m, 4H, NCH$_2$), 3.48 (s, 2H, NCH$_2$), 4.27 (t, 2H, OCH$_2$), 4.60 (s, 2H, OCH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 36

Preparation of 2-(4-methylbenzoyl)-3-[4-(dimethylaminoethoxy)phenyl]-6,7-dihydrogen-5H-furo[3,2-g]chromene Following the method of Example 13, 0.24 g of 2-(4-methylbenzoyl)-3-[4-(dimethylaminoethoxy)phenyl]-6,7-dihydrogen-5H-furo[3,2-g]chromene was obtained, with a yield of 50% and ESI-MS m/z (M+1) 456.21; $^1$HNMR (600 MHz, CDCl$_3$, δ: ppm): 2.05 (t, 2H, CH$_2$), 2.90 (t, 2H, CH$_2$), 3.05 (s, 6H, NCH$_3$), 3.15 (t, 2H, NCH$_2$), 4.27 (t, 2H, OCH$_2$), 4.60 (s, 2H, OCH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 37

Preparation of 2-(4-methylbenzoyl)-3-[4-(morpholine-2-oxo-ethoxy)phenyl]-6,7-dihydrogen-5H-furo[3,2-g]chromene Following the method of Example 13, 0.24 g of 2-(4-methylbenzoyl)-3-[4-(morpholine-2-oxo-ethoxy)phenyl]-6,7-dihydrogen-5H-furo[3,2-g]chromene was obtained, with a yield of 50% and ESI-MS m/z (M+1) 512.21; $^1$HNMR (600 MHz, CDCl$_3$, δ: ppm): 2.05 (t, 2H, CH$_2$), 2.90 (t, 2H, CH$_2$), 3.60-3.72 (m, 8H), 4.27 (t, 2H, OCH$_2$), 4.71 (s, 2H, OCH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 38

Preparation of 2-(4-methylbenzoyl)-3-[4-(piperidine-2-oxo-ethoxy)phenyl]-6,7-dihydrogen-5H-furo[3,2-g]chromene Following the method of Example 13, 0.24 g of 2-(4-methylbenzoyl)-3-[4-(piperidine-2-oxo-ethoxy)phenyl]-6,7-dihydrogen-5H-furo[3,2-g]chromene was obtained, with a yield of 50% and ESI-MS m/z (M+1) 510.22; $^1$HNMR (600 MHz, CDCl$_3$, δ: ppm): 1.58-1.68 (m, 6H), 2.05 (t, 2H, CH$_2$), 2.91 (t, 2H, CH$_2$), 3.49 (m, 2H, NCH$_2$), 3.59 (m, 2H, NCH$_2$), 4.27 (t, 2H, OCH$_2$), 4.69 (s, 2H, OCH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 39

Preparation of 2-(4-methylbenzoyl)-3-[4-(diethylamino-2-oxo-ethoxy)phenyl]-6,7-dihydrogen-5H-furo[3,2-g]chromene Following the method of Example 13, 0.24 g of 2-(4-methylbenzoyl)-3-[4-(diethylamino-2-oxo-ethoxy)phenyl]-6,7-dihydrogen-5H-furo[3,2-g]chromene was obtained, with a yield of 50% and ESI-MS m/z (M+1) 498.22; $^1$HNMR (600 MHz, CDCl$_3$, δ: ppm): 1.17 (t, 3H, CH$_3$), 1.24 (t, 3H, CH$_3$), 2.05 (t, 2H, CH$_2$), 2.91 (t, 2H, CH$_2$), 3.38-3.44 (m, 4H, NCH$_2$), 4.27 (t, 2H, OCH$_2$), 4.68 (s, 2H, OCH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 40

Preparation of 2-(4-methylbenzoyl)-3-[4-(dimethylamino-2-oxo-ethoxy)phenyl]-6,7-dihydrogen-5H-furo[3,2-g]chromene Following the method of Example 13, 0.24 g of 2-(4-methylbenzoyl)-3-[4-(dimethylamino-2-oxo-ethoxy)phenyl]-6,7-dihydrogen-5H-furo[3,2-g]chromene was obtained, with a yield of 50% and ESI-MS m/z (M+1) 470.19; $^1$HNMR (600 MHz, CDCl$_3$, δ: ppm): 2.05 (t, 2H, CH$_2$), 2.91 (t, 2H, CH$_2$), 3.01 (s, 3H, NCH$_3$), 3.11 (s, 3H, NCH$_3$), 4.27 (t, 2H, OCH$_2$), 4.71 (s, 2H, OCH$_2$), 6.80 (dd, 2H, ArH, J=7.0 Hz, J=1.9 Hz), 7.41-7.47 (m, 3H, ArH), 7.55 (s, 1H, ArH), 7.68 (dd, 2H, ArH, J=7.0 Hz, J=1.9 Hz), 7.77 (dd, 2H, ArH, J=7.0 Hz, J=1.9 Hz).

Example 41

Preparation of 2-(4-bromobenzoyl)-3-[4-(morpholinoethoxy)phenyl]-6,7-dihydrogen-5H-furo[3,2-g]chromene Following the method of Example 13, 0.24 g of 2-(4-bromobenzoyl)-3-[4-(morpholinoethoxy)phenyl]-6,7-dihydrogen-5H-furo[3,2-g]chromene was obtained, with a yield of 50% and ESI-MS m/z (M+1) 562.12; $^1$HNMR (600 MHz, CDCl$_3$, δ: ppm): 2.05 (t, 2H, CH$_2$), 2.91 (t, 2H, CH$_2$), 3.06 (t, 2H, NCH$_2$), 3.44 (s, 2H, NCH$_2$), 3.55 (m, 2H, NCH$_2$), 4.01 (m, 2H, OCH$_2$), 4.26-4.32 (m, 4H, OCH$_2$), 4.64 (s, 2H, OCH$_2$), 6.86 (dd, 2H, ArH, J=7.0 Hz, J=1.9 Hz), 7.47 (s, 1H, ArH), 7.55 (s, 1H, ArH), 7.62-7.65 (m, 4H, ArH), 7.79 (dd, 2H, ArH, J=7.0 Hz, J=1.9 Hz).

Example 42

Preparation of 2-(4-bromobenzoyl)-3-[4-(piperidinoethoxy)phenyl]-6,7-dihydrogen-5H-furo[3,2-g]chromene Following the method of Example 13, 0.24 g of 2-(4-bromobenzoyl)-3-[4-(piperidinoethoxy)phenyl]-6,7-dihydrogen-5H-furo[3,2-g]chromene was obtained, with a yield of 50% and ESI-MS m/z (M+1) 560.14; $^1$HNMR (600 MHz, CDCl$_3$, δ: ppm): 1.45 (m, 2H, CH$_2$), 1.59-1.63 (m, 4H, CH$_2$), 2.05 (t, 2H, CH$_2$), 2.50 (s, 4H, NCH$_2$), 2.77 (t, 2H, NCH$_2$), 2.90 (t, 2H, CH$_2$), 4.13 (t, 2H, OCH$_2$), 4.26 (t, 2H, OCH$_2$), 6.86 (dd, 2H, ArH, J=7.0 Hz, J=1.9 Hz), 7.47 (s, 1H, ArH), 7.55 (s, 1H, ArH), 7.62-7.65 (m, 4H, ArH), 7.79 (dd, 2H, ArH, J=7.0 Hz, J=1.9 Hz).

Example 43

Preparation of 2-(4-bromobenzoyl)-3-[4-(diethylaminoethoxy)phenyl]-6,7-dihydrogen-5H-furo[3,2-g]chromene Following the method of Example 13, 0.24 g of 2-(4-bromobenzoyl)-3-[4-(diethylaminoethoxy)phenyl]-6,7-dihydrogen-5H-furo[3,2-g]chromene was obtained, with a yield of 50% and ESI-MS m/z (M+1) 548.14; $^1$HNMR (600 MHz, CDCl$_3$, δ: ppm): 1.48 (t, 6H, CH$_3$), 2.05 (t, 2H, CH$_2$), 2.90 (t, 2H, CH$_2$), 3.24-3.33 (m, 4H, NCH$_2$), 3.48 (s, 2H, NCH$_2$), 4.27 (t, 2H, OCH$_2$), 4.60 (s, 2H, OCH$_2$), 6.86 (dd, 2H, ArH, J=7.0 Hz, J=1.9 Hz), 7.47 (s, 1H, ArH), 7.55 (s, 1H, ArH), 7.62-7.65 (m, 4H, ArH), 7.79 (dd, 2H, ArH, J=7.0 Hz, J=1.9 Hz).

Example 44

Preparation of 2-(4-bromobenzoyl)-3-[4-(dimethylaminoethoxy)phenyl]-6,7-dihydrogen-5H-furo[3,2-q]chromene Following the method of Example 13, 0.24 g of 2-(4-bromobenzoyl)-3-[4-(dimethylaminoethoxy)phenyl]-6,7-dihydrogen-5H-furo[3,2-g]chromene was obtained, with a yield of 50% and ESI-MS m/z (M+1) 520.10; $^1$HNMR (600 MHz, CDCl$_3$, δ: ppm): 2.05 (t, 2H, CH$_2$), 2.90 (t, 2H, CH$_2$), 3.05 (s, 6H, NCH$_3$), 3.15 (t, 2H, NCH$_2$), 4.27 (t, 2H, OCH$_2$), 4.60 (s, 2H, OCH$_2$), 6.86 (dd, 2H, ArH, J=7.0 Hz, J=1.9 Hz), 7.47 (s, 1H, ArH), 7.55 (s, 1H, ArH), 7.62-7.65 (m, 4H, ArH), 7.79 (dd, 2H, ArH, J=7.0 Hz, J=1.9 Hz).

Example 45

Preparation of 2-(4-bromobenzoyl)-3-[4-(morpholine-2-oxo-ethoxy)phenyl]-6,7-dihydrogen-5H-furo[3,2-g]chromene Following the method of Example 13, 0.24 g of 2-(4-bromobenzoyl)-3-[4-(morpholine-2-oxo-ethoxy)phenyl]-6,7-dihydrogen-5H-furo[3,2-g]chromene was obtained, with a yield of 50% and ESI-MS m/z (M+1) 576.09; $^1$HNMR (600 MHz, CDCl$_3$, δ: ppm): 2.05 (t, 2H, CH$_2$), 2.90 (t, 2H, CH$_2$), 3.60-3.72 (m, 8H), 4.27 (t, 2H, OCH$_2$), 4.71 (s, 2H, OCH$_2$), 6.86 (dd, 2H, ArH, J=7.0 Hz, J=1.9 Hz), 7.47 (s, 1H, ArH), 7.55 (s, 1H, ArH), 7.62-7.65 (m, 4H, ArH), 7.79 (dd, 2H, ArH, J=7.0 Hz, J=1.9 Hz).

Example 46

Preparation of 2-(4-bromobenzoyl)-3-[4-(piperidine-2-oxo-ethoxy)phenyl]-6,7-dihydrogen-5H-furo[3,2-g]chromene Following the method of Example 13, 0.24 g of 2-(4-bromobenzoyl)-3-[4-(piperidine-2-oxo-ethoxy)phenyl]-6,7-dihydrogen-5H-furo[3,2-g]chromene was obtained, with a yield of 50% and ESI-MS m/z (M+1) 575.12; $^1$HNMR (600 MHz, CDCl$_3$, δ: ppm): 1.58-1.68 (m, 6H), 2.05 (t, 2H, CH$_2$), 2.91 (t, 2H, CH$_2$), 3.49 (m, 2H, NCH$_2$), 3.59 (m, 2H, NCH$_2$), 4.27 (t, 2H, OCH$_2$), 4.69 (s, 2H, OCH$_2$), 6.86 (dd, 2H, ArH, J=7.0 Hz, J=1.9 Hz), 7.47 (s, 1H, ArH), 7.55 (s, 1H, ArH), 7.62-7.65 (m, 4H, ArH), 7.79 (dd, 2H, ArH, J=7.0 Hz, J=1.9 Hz).

Example 47

Preparation of 2-(4-bromobenzoyl)-3-[4-(dimethylamino-2-oxo-ethoxy)phenyl]-6,7-dihydrogen-5H-furo[3,2-g]chromene Following the method of Example 13, 0.24 g of 2-(4-bromobenzoyl)-3-[4-(dimethylamino-2-oxo-ethoxy)phenyl]-6,7-dihydrogen-5H-furo[3,2-g]chromene was obtained, with a yield of 50% and ESI-MS m/z (M+1) 534.08; $^1$HNMR (600 MHz, CDCl$_3$, δ: ppm): 2.05 (t, 2H, CH$_2$), 2.91 (t, 2H, CH$_2$), 3.01 (s, 3H, NCH$_3$), 3.11 (s, 3H, NCH$_3$), 4.27 (t, 2H, OCH$_2$), 4.71 (s, 2H, OCH$_2$), 6.86 (dd, 2H, ArH, J=7.0

J=1.9 Hz), 7.47 (s, 1H, ArH), 7.55 (s, 1H, ArH), 7.62-7.65 (m, 4H, ArH), 7.79 (dd, 2H, ArH, J=7.0 Hz, J=1.9 Hz).

Example 48

Preparation of 2-[4-(piperidinoethoxy)benzoyl]-3-(4-methoxyphenyl)-6,7-dihydrogen-5H-furo[3,2-g]chromene Following the method of Example 13, 0.24 g of 2-[4-(piperidinoethoxy)benzoyl]-3-(4-methoxyphenyl)-6,7-dihydrogen-5H-furo[3,2-g]chromene was obtained, with a yield of 50% and ESI-MS m/z (M+1) 512.24; $^1$HNMR (600 MHz, CDCl$_3$, δ: ppm): 1.45 (m, 2H, CH$_2$), 1.59-1.63 (m, 4H, CH$_2$), 2.05 (t, 2H, CH$_2$), 2.50 (s, 4H, NCH$_2$), 2.77 (t, 2H, NCH$_2$), 2.90 (t, 2H, CH$_2$), 4.13 (t, 2H, OCH$_2$), 4.26 (t, 2H, OCH$_2$), 6.89 (dd, 2H, ArH, J=7.0 Hz, J=1.9 Hz), 7.05 (dd, 2H, ArH, J=7.0 Hz, J=1.9 Hz), 7.47 (s, 1H, ArH), 7.55 (s, 1H, ArH), 7.68-7.72 (m, 4H, ArH).

Example 49

Preparation of 2-[4-(morpholinoethoxy)benzoyl]-3-(4-methoxyphenyl)-6,7-dihydrogen-5H-furo[3,2-g]chromene Following the method of Example 13, 0.24 g of 2-[4-(morpholinoethoxy)benzoyl]-3-(4-methoxyphenyl)-6,7-dihydrogen-5H-furo[3,2-g]chromene was obtained, with a yield of 50% and ESI-MS m/z (M+1) 514.22; $^1$HNMR (600 MHz, CDCl$_3$, δ: ppm): 2.05 (t, 2H, CH$_2$), 2.91 (t, 2H, CH$_2$), 3.06 (t, 2H, NCH$_2$), 3.44 (s, 2H, NCH$_2$), 3.55 (m, 2H, NCH$_2$), 4.01 (m, 2H, OCH$_2$), 4.26-4.32 (m, 4H, OCH$_2$), 4.64 (s, 2H, OCH$_2$), 6.89 (dd, 2H, ArH, J=7.0 Hz, J=1.9 Hz), 7.05 (dd, 2H, ArH, J=7.0 Hz, J=1.9 Hz), 7.47 (s, 1H, ArH), 7.55 (s, 1H, ArH), 7.68-7.72 (m, 4H, ArH).

Example 50

Preparation of 2-[4-(diethylaminoethoxy)benzoyl]-3-(4-methoxyphenyl)-6,7-dihydrogen-5H-furo[3,2-g]chromene Following the method of Example 13, 0.24 g of 2-[4-(diethylaminoethoxy)benzoyl]-3-(4-methoxyphenyl)-6,7-dihydrogen-5H-furo[3,2-g]chromene was obtained, with a yield of 50% and ESI-MS m/z (M+1) 500.24; $^1$HNMR (600 MHz, CDCl$_3$, δ: ppm): 1.48 (t, 6H, CH$_3$), 2.05 (t, 2H, CH$_2$), 2.90 (t, 2H, CH$_2$), 3.24-3.33 (m, 4H, NCH$_2$), 3.48 (s, 2H, NCH$_2$), 4.27 (t, 2H, OCH$_2$), 4.60 (s, 2H, OCH$_2$), 6.89 (dd, 2H, ArH, J=7.0 Hz, J=1.9 Hz), 7.05 (dd, 2H, ArH, J=7.0 Hz, J=1.9 Hz), 7.47 (s, 1H, ArH), 7.55 (s, 1H, ArH), 7.68-7.72 (m, 4H, ArH).

Example 51

Preparation of 2-[4-(diethylamino-2-oxo-ethoxy)benzoyl]-3-(4-methoxyphenyl)-6,7-dihydrogen-5H-furo[3,2-g]chromene Following the method of Example 13, 0.24 g of 2-[4-(diethylamino-2-oxo-ethoxy)benzoyl]-3-(4-methoxyphenyl)-6,7-dihydrogen-5H-furo[3,2-g]chromene was obtained, with a yield of 50% and ESI-MS m/z (M+1) 514.22; $^1$HNMR (600 MHz, CDCl$_3$, δ: ppm): 1.17 (t, 3H, CH$_3$), 1.24 (t, 3H, CH$_3$), 2.05 (t, 2H, CH$_2$), 2.91 (t, 2H, CH$_2$), 3.38-3.44 (m, 4H, NCH$_2$), 4.27 (t, 2H, OCH$_2$), 4.68 (s, 2H, OCH$_2$), 6.89 (dd, 2H, ArH, J=7.0 Hz, J=1.9 Hz), 7.05 (dd, 2H, ArH, J=7.0 Hz, J=1.9 Hz), 7.47 (s, 1H, ArH), 7.55 (s, 1H, ArH), 7.68-7.72 (m, 4H, ArH).

Example 52

Preparation of 2-[4-(piperidine-2-oxo-ethoxy)benzoyl]-3-(4-methoxyphenyl)-6,7-dihydrogen-5H-furo[3,2-g]chromene Following the method of Example 13, 0.24 g of 2-[4-(piperidine-2-oxo-ethoxy)benzoyl]-3-(4-methoxyphenyl)-6,7-dihydrogen-5H-furo[3,2-g]chromene was obtained, with a yield of 50% and ESI-MS m/z (M+1) 526.22; $^1$HNMR (600 MHz, CDCl$_3$, δ: ppm): 1.58-1.68 (m, 6H), 2.05 (t, 2H, CH$_2$), 2.91 (t, 2H, CH$_2$), 3.49 (m, 2H, NCH$_2$), 3.59 (m, 2H, NCH$_2$), 4.27 (t, 2H, OCH$_2$), 4.69 (s, 2H, OCH$_2$), 6.89 (dd, 2H, ArH, J=7.0 Hz, J=1.9 Hz), 7.05 (dd, 2H, ArH, J=7.0 Hz, J=1.9 Hz), 7.47 (s, 1H, ArH), 7.55 (s, 1H, ArH), 7.68-7.72 (m, 4H, ArH).

Example 53

Preparation of 2-[4-(morpholine-2-oxo-ethoxy)benzoyl]-3-(4-methoxyphenyl)-6,7-dihydrogen-5H-furo[3,2-g]chromene Following the method of Example 13, 0.24 g of 2-[4-(morpholine-2-oxo-ethoxy)benzoyl]-3-(4-methoxyphenyl)-6,7-dihydrogen-5H-furo[3,2-g]chromene was obtained, with a yield of 50% and ESI-MS m/z (M+1) 528.19; $^1$HNMR (600 MHz, CDCl$_3$, δ: ppm): 2.05 (t, 2H, CH$_2$), 2.90 (t, 2H, CH$_2$), 3.60-3.72 (m, 8H), 4.27 (t, 2H, OCH$_2$), 4.71 (s, 2H, OCH$_2$), 6.89 (dd, 2H, ArH, J=7.0 Hz, J=1.9 Hz), 7.05 (dd, 2H, ArH, J=7.0 Hz, J=1.9 Hz), 7.47 (s, 1H, ArH), 7.55 (s, 1H, ArH), 7.68-7.72 (m, 4H, ArH).

Example 54

Preparation of 2-[4-(dimethylamino-2-oxo-ethoxy)benzoyl]-3-(4-methoxyphenyl)-6,7-dihydrogen-5H-furo[3,2-g]chromene Following the method of Example 13, 0.24 g of 2-[4-(dimethylamino-2-oxo-ethoxy)benzoyl]-3-(4-methoxyphenyl)-6,7-dihydrogen-5H-furo[3,2-g]chromene was obtained, with a yield of 50% and ESI-MS m/z (M+1) 486.18; $^1$HNMR (600 MHz, CDCl$_3$, δ: ppm): 2.05 (t, 2H, CH$_2$), 2.91 (t, 2H, CH$_2$), 3.01 (s, 3H, NCH$_3$), 3.11 (s, 3H, NCH$_3$), 4.27 (t, 2H, OCH$_2$), 4.71 (s, 2H, OCH$_2$), 6.89 (dd, 2H, ArH, J=7.0 Hz, J=1.9 Hz), 7.05 (dd, 2H, ArH, J=7.0 Hz, J=1.9 Hz), 7.47 (s, 1H, ArH), 7.55 (s, 1H, ArH), 7.68-7.72 (m, 4H, ArH).

Example 55

Preparation of 2-[4-(piperidinoethoxy)benzoyl]-3-(4-hydroxyphenyl)-6,7-dihydrogen-5H-furo[3,2-g]chromene Following the method of Example 13, 0.24 g of 2-[4-(piperidinoethoxy)benzoyl]-3-(4-hydroxyphenyl)-6,7-dihydrogen-5H-furo[3,2-g]chromene was obtained, with a yield of 50% and ESI-MS m/z (M+1) 498.22; $^1$HNMR (600 MHz, CDCl$_3$, δ: ppm): 1.45 (m, 2H, CH$_2$), 1.59-1.63 (m, 4H, CH$_2$), 2.05 (t, 2H, CH$_2$), 2.50 (s, 4H, NCH$_2$), 2.77 (t, 2H, NCH$_2$), 2.90 (t, 2H, CH$_2$), 4.13 (t, 2H, OCH$_2$), 4.26 (t, 2H, OCH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Example 56

Preparation of 2-[4-(diethylaminoethoxy)benzoyl]-3-(4-hydroxyphenyl)-6,7-dihydrogen-5H-furo[3,2-g]chromene Following the method of Example 13, 0.24 g of 2-[4-(diethylaminoethoxy)benzoyl]-3-(4-hydroxyphenyl)-6,7-dihydrogen-5H-furo[3,2-g]chromene was obtained, with a yield of 50% and ESI-MS m/z (M+1) 486.22; $^1$HNMR (600 MHz, CDCl$_3$, δ: ppm): 1.48 (t, 6H, CH$_3$), 2.05 (t, 2H, CH$_2$), 2.90 (t, 2H, CH$_2$), 3.24-3.33 (m, 4H, NCH$_2$), 3.48 (s, 2H, NCH$_2$), 4.27 (t, 2H, OCH$_2$), 4.60 (s, 2H, OCH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Example 57

Preparation of 2-[4-(morpholinoethoxy)benzoyl]-3-(4-hydroxyphenyl)-6,7-dihydrogen-5H-furo[3,2-g]chromene Following the method of Example 13, 0.24 g of 2-[4-(morpholinoethoxy)benzoyl]-3-(4-hydroxyphenyl)-6,7-dihydrogen-5H-furo[3,2-g]chromene was obtained, with a yield of 50% and ESI-MS m/z (M+1) 500.2; $^1$HNMR (600 MHz, CDCl$_3$, δ: ppm): 2.05 (t, 2H, CH$_2$), 2.91 (t, 2H, CH$_2$), 3.06 (t, 2H, NCH$_2$), 3.44 (s, 2H, NCH$_2$), 3.55 (m, 2H, NCH$_2$), 4.01 (m, 2H, OCH$_2$), 4.26-4.32 (m, 4H, OCH$_2$), 4.64 (s, 2H, OCH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Example 58

Preparation of 2-[4-(dimethylaminoethoxy)benzoyl]-3-(4-hydroxyphenyl)-6,7-dihydrogen-5H-furo[3,2-g]chromene Following the method of Example 13, 0.24 g of 2-[4-(dimethylaminoethoxy)benzoyl]-3-(4-hydroxyphenyl)-6,7-dihydrogen-5H-furo[3,2-g]chromene was obtained, with a yield of 50% and ESI-MS m/z (M+1) 458.19; $^1$HNMR (600 MHz, CDCl$_3$, δ: ppm): 2.05 (t, 2H, CH$_2$), 2.90 (t, 2H, CH$_2$), 3.05 (s, 6H, NCH$_3$), 3.15 (t, 2H, NCH$_2$), 4.27 (t, 2H, OCH$_2$), 4.60 (s, 2H, OCH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Example 59

Preparation of 2-[4-(dimethylaminoethoxy)benzoyl]-3-phenyl-6,7-dihydrogen-5H-furo[3,2-q]chromene Following the method of Example 13, 0.24 g of 2-[4-(dimethylaminoethoxy)benzoyl]-3-phenyl-6,7-dihydrogen-5H-furo[3,2-g]chromene was obtained, with a yield of 50% and ESI-MS m/z (M+1) 442.19; $^1$HNMR (600 MHz, CDCl$_3$, δ: ppm): 2.05 (t, 2H, CH$_2$), 2.90 (t, 2H, CH$_2$), 3.05 (s, 6H, NCH$_3$), 3.15 (t, 2H, NCH$_2$), 4.27 (t, 2H, OCH$_2$), 4.60 (s, 2H, OCH$_2$), 6.94 (dd, 2H, ArH, J=9.0 Hz, J=3.0 Hz), 7.01 (s, 1H, ArH), 7.31 (s, 1H, ArH), 7.34 (m, 2H, ArH), 7.40-7.46 (m, 3H, ArH), 7.82 (dd, 2H, ArH, J=9.0 Hz, J=3.0 Hz).

Example 60

Preparation of 2-[4-(piperidine-2-oxo-ethoxy)benzoyl]-3-(4-hydroxyphenyl)-6,7-dihydrogen-5H-furo[3,2-g]chromene Following the method of Example 13, 0.24 g of 2-[4-(piperidine-2-oxo-ethoxy)benzoyl]-3-(4-hydroxyphenyl)-6,7-dihydrogen-5H-furo[3,2-g]chromene was obtained, with a yield of 50% and ESI-MS m/z (M+1) 512.2; $^1$HNMR (600 MHz, CDCl$_3$, δ: ppm): 1.58-1.68 (m, 6H), 2.05 (t, 2H, CH$_2$), 2.91 (t, 2H, CH$_2$), 3.49 (m, 2H, NCH$_2$), 3.59 (m, 2H, NCH$_2$), 4.27 (t, 2H, OCH$_2$), 4.69 (s, 2H, OCH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Example 61

Preparation of 2-[4-(piperidine-2-oxo-ethoxy)benzoyl]-3-[4-(piperidine-2-oxo-ethoxy)phenyl]-6,7-dihydrogen-5H-furo[3,2-g]chromene Following the method of Example 13, 0.24 g of 2-[4-(piperidine-2-oxo-ethoxy)benzoyl]-3-[4-(piperidine-2-oxo-ethoxy)phenyl]-6,7-dihydrogen-5H-furo[3,2-g]chromene was obtained, with a yield of 50% and ESI-MS m/z (M+1) 637.28; $^1$HNMR (600 MHz, CDCl$_3$, δ: ppm): 1.58-1.68 (m, 12H), 2.05 (t, 2H, CH$_2$), 2.91 (t, 2H, CH$_2$), 3.49 (m, 4H, NCH$_2$), 3.59 (m, 4H, NCH$_2$), 4.27 (t, 2H, OCH$_2$), 4.69 (s, 4H, OCH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Example 62

Preparation of 2-[4-(diethylamino-2-oxo-ethoxy)benzoyl]-3-(4-hydroxyphenyl)-6,7-dihydrogen-5H-furo[3,2-g]chromene Following the method of Example 13, 0.24 g of 2-[4-(diethylamino-2-oxo-ethoxy)benzoyl]-3-(4-hydroxyphenyl)-6,7-dihydrogen-5H-furo[3,2-g]chromene was obtained, with a yield of 50% and ESI-MS m/z (M+1) 500.2; $^1$HNMR (600 MHz, CDCl$_3$, δ: ppm): 1.17 (t, 3H, CH$_3$), 1.24 (t, 3H, CH$_3$), 2.05 (t, 2H, CH$_2$), 2.91 (t, 2H, CH$_2$), 3.38-3.44 (m, 4H, NCH$_2$), 4.27 (t, 2H, OCH$_2$), 4.68 (s, 2H, OCH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Example 63

Preparation of 2-[4-(diethylamino-2-oxo-ethoxy)benzoyl]-3-[4-(diethylamino-2-oxo-ethoxy)phenyl]-6,7-dihydrogen-5H-furo[3,2-g]chromene Following the method of Example 13, 0.24 g of 2-[4-(diethylamino-2-oxo-ethoxy)benzoyl]-3-[4-(diethylamino-2-oxo-ethoxy)phenyl]-6,7-dihydrogen-5H-furo[3,2-g]chromene was obtained, with a yield of 50% and ESI-MS m/z (M+1) 613.28; $^1$HNMR (600 MHz, CDCl$_3$, δ: ppm): 1.17 (t, 6H, CH$_3$), 1.24 (t, 6H, CH$_3$), 2.05 (t, 2H, CH$_2$), 2.91 (t, 2H, CH$_2$), 3.38-3.44 (m, 8H, NCH$_2$), 4.27 (t, 2H, OCH$_2$), 4.68 (s, 4H, OCH$_2$), 6.86-6.89 (m, 4H, ArH), 7.47 (s, 1H, ArH), 7.55

(s, 1H, ArH), 7.62 (dd, 2H, ArH, J=7.0 Hz, J=1.9 Hz), 7.72 (dd, 2H, ArH, J=7.0 Hz, J=1.9 Hz).

Example 64

Preparation of 2-[4-(dimethylamino-2-oxo-ethoxy)benzoyl]-3-(4-hydroxyphenyl)-6,7-dihydrogen-5H-furo[3,2-g]chromene Following the method of Example 13, 0.24 g of 2-[4-(dimethylamino-2-oxo-ethoxy)benzoyl]-3-(4-hydroxyphenyl)-6,7-dihydrogen-5H-furo[3,2-g]chromene was obtained, with a yield of 50% and ESI-MS m/z (M+1) 472.17; $^1$HNMR (600 MHz, CDCl$_3$, δ: ppm): 2.05 (t, 2H, CH$_2$), 2.91 (t, 2H, CH$_2$), 3.01 (s, 3H, NCH$_3$), 3.11 (s, 3H, NCH$_3$), 4.27 (t, 2H, OCH$_2$), 4.71 (s, 2H, OCH$_2$), 6.86-6.89 (m, 4H, ArH), 7.47 (s, 1H, ArH), 7.55 (s, 1H, ArH), 7.62 (dd, 2H, ArH, J=7.0 Hz, J=1.9 Hz), 7.72 (dd, 2H, ArH, J=7.0 Hz, J=1.9 Hz).

Pharmaceutical Compositions

In the following preparations, the "active component" means the compound represented by formula I, or a salt or solvate thereof.

Example 65

Gelatin Capsules

| Components | Mass (mg/capsule) |
|---|---|
| active component | 0.1-1000 |
| starch, NF | 0-650 |
| flowable starch powder | 0-650 |
| siloxane fluid of 350 centistoke | 0-15 |

Example 66

Tablets

| Components | Mass (mg/tablet) |
|---|---|
| active component | 2.5-1000 |
| microcrystalline cellulose | 200-650 |
| silicon dioxide | 10-650 |
| stearic acid | 5-15 |

Example 67

Tablets

| Components | Mass (mg/tablet) |
|---|---|
| active component | 25-1000 |
| starch | 45 |
| microcrystalline cellulose | 35 |
| polyvinylpyrrolidone (as 10% aqueous solution) | 4 |
| carboxymethylcellulose sodium | 4.5 |
| magnesium stearate | 0.5 |
| talc | 1 |

The active component, starch and cellulose were passed through a 45-mesh U.S. sieve and mixed thoroughly. The resultant powder was mixed with polyvinylpyrrolidone, and then passed through a 14-mesh U.S. sieve. The obtained particles were dried at 50-60° C., and then passed through an 18-mesh U.S. sieve. Carboxymethylcellulose sodium, magnesium stearate and talc were first passed through a 60-mesh U.S. sieve, and added to and mixed with the above particles, then pressed into tablets in a tabletting machine.

Example 68

Suspension

| Components | Mass (mg/5 mL) |
|---|---|
| active component | 0.1-1000 mg |
| carboxymethylcellulose sodium | 50 mg |
| syrup | 1.25 mg |
| benzoic acid solution | 0.1 mL |
| flavoring agent | q.l. |
| colorant | q.l. |
| add purified water to | 5 mL |

The medicament was passed through a 45-mesh U.S. sieve, and mixed with carboxymethylcellulose sodium and syrup, so as to form a homogeneous paste. The benzoic acid solution, flavoring agent and colorant were diluted with some water, and added to the paste under agitation. Then sufficient water was added to make up to the desired volume.

Example 69

Aerosol

| Components | Mass (w %) |
|---|---|
| active component | 0.25 |
| ethanol | 25.75 |
| propellant 22(monochlorodifluoromethane) | 70 |

The active component was mixed with ethanol, then the resultant mixture was added to a part of propellant 22, cooled down to 30° C., and transferred into a container. Subsequently, a desired amount of the obtained mixture was placed into a stainless steel container and further diluted with the rest propellant. A valve device was installed afterward.

Example 70

Suppository

| Components | Mass (mg/suppository) |
|---|---|
| active component | 250 |
| saturated fatty glycerides | 2000 |

The active component was passed through a 60-mesh U.S. sieve, and suspended in pre-melted saturated fatty glycerides.

Then the resultant mixture was poured into a standard suppository mold with a 2 g chamber, and cooled down.

Example 71

Injectable Preparation

| Components | Mass |
|---|---|
| active component | 50 mg |
| isotonic salt solution | 1000 mL |

The above solution was administered to a patient by intravenous injection, with a rate of about 1 mL/min.

Pharmacological-Pharmacodynamical Experiments

Example 72

Estrogen Receptor Binding Experiment

The estrogen receptor-ligand binding experiment was designed to utilize Scintillation Proximity Assay, tritium-containing estradiol, and recombinantly expressed estrogen receptor. Full-length recombinant human ER-α and ER-β proteins were produced in an expression system of baculovirus. ER-α and ER-β extractions were diluted 1:400 in phosphate-buffered saline containing 6 mM α-monothioglycerol. An aliquot of 200 μL diluted receptor preparation was added to each well of a 96-well Flashplate. The plate was covered by Saran Wrap, and incubated at 4° C. overnight.

The next morning, an aliquot of 20 μL phosphate-buffered saline containing 10% Bovine Serum Albumin was added to each well of the 96-well plate, and the plate was incubated at 4° C. for 2 h. Then the plated was washed with 200 μL buffer containing 20 mM Tris (pH7.2), 1 mM EDTA, 10% glycerin, 50 mM KCl and 6 mM α-monothioglycerol. In order to conduct the assay in the plate coated with these receptors, 178 μL of the same buffer was added to each well of the 96-well plate. Subsequently, 20 μL of 10 nM 3H-estradiol solution was added to each well of the 96-well plate.

The test compound was evaluated within a concentration range of 0.01 nM~1000 nM. The stock solution of the test compound was prepared in 100% DMSO with a concentration of 100× final concentration desired for the test in the experiment. The amount of DMSO should not be more than 1% in each test well of the 96-well plate. An aliquot of 2 μL test compound prepared in 100% DMSO was added to the test lastly. The plate were sealed, and balanced at room temperature for 3 h. The plate was counted using a scintillation counter suitable for a 96-well plate device.

Table of the inhibition ratios in the estrogen receptor binding experiments for some samples (n = 2):

| Samples | $IC_{50}$ (μM) |
|---|---|
| 2-[4-(dimethylamino-2-oxo-ethoxy)benzoyl]-3-(4-hydroxyphenyl)-6,7-dihydrogen-5H-furo[3,2-g]chromene | 5.8 |
| 2-[4-(diethylamino-2-oxo-ethoxy)benzoyl]-3-(4-hydroxyphenyl)-6,7-dihydrogen-5H-furo[3,2-g]chromene | 26.2 |
| 2-[4-(piperidine-2-oxo-ethoxy)benzoyl]-3-(4-hydroxyphenyl)-6,7-dihydrogen-5H-furo[3,2-g]chromene | 4.5 |
| 2-[4-(morpholine-2-oxo-ethoxy)benzoyl]-3-(4-hydroxyphenyl)-6,7-dihydrogen-5H-furo[3,2-g]chromene | 11.7 |

-continued

Table of the inhibition ratios in the estrogen receptor binding experiments for some samples (n = 2):

| Samples | $IC_{50}$ (μM) |
|---|---|
| 2-[4-(dimethylaminoethoxy)benzoyl]-3-(4-hydroxyphenyl)-6,7-dihydrogen-5H-furo[3,2-g]chromene | 34.6 |
| 2-[4-(diethylaminoethoxy)benzoyl]-3-(4-hydroxyphenyl)-6,7-dihydrogen-5H-furo[3,2-g]chromene | 7.1 |

The compounds of Examples 1-64 exhibited a binding affinity with ERα within a range of $IC_{50}$=75~10000 nm, and a binding affinity with ERR within a range of $IC_{50}$=5~250 nm. The result of the above standard pharmacological test showed that the compounds of the invention are estrogen compounds, and some compounds have a strongly preferred affinity for ERα receptor. The affinities of compounds of the invention varied from the preferred affinities for ERα over ERβ to almost comparable affinities for both receptors. As a result, the compounds of the invention have all types of activities which are at least partially based on the selective properties of their affinities for the receptors. In addition, due to the difference among each new receptor-ligand complex, it has different interaction with all co-regulatory proteins as well. The compounds of the invention will exhibit different activities depending on their cellular environments. For instance, a certain compound can act as an estrogen agonist in some types of cells, but as an antagonist in other tissues. The compounds that have the above activities are normally named as SERM (selective estrogen receptor modulator). However, unlike most estrogens, many SERMs do not increase the wet weight of uterus. These compounds have an anti-estrogen activity in uterus, thus can completely antagonize the trophic activity of an estrogen agonist in uterus tissues. However, these compounds act as estrogen agonists in bone, cardiovascular and central nervous systems.

Because these compounds have the tissue-selective property mentioned above, they can be used for treating or preventing pathological conditions or syndromes caused by or related with estrogen deficiency (in some tissues e.g. bone and cardiovascular tissues) or estrogen excess (in uterus or mammary gland). Moreover, beyond the above cell specific modulations, the compounds of the invention are also potentially agonists for a certain type of receptor but antagonists for another type of receptor. For example, the compounds of the invention are antagonists for ERβ; but agonists for ERα. Such estrogen receptor selective agonist/antagonist activities endue this series of compounds with pharmacologically significant different estrogen activities.

The activity features of the inventive compounds can be conveniently tested by standard pharmacological assays. Several typical testing procedures are described briefly as follows. All the compounds according to the invention exhibited biological activities similar to those of raloxifene.

Example 73

Procedure of Uterotrophic/Anti-Uterotrophic Assay in Rat

The estrogen and anti-estrogen properties of the compound can be tested in the uterotrophic assay (4 days) in juvenile rats. Immature rats (Sprague-Dawley rats) (female, 18 days old) were divided into 6 test groups. All these animals were i.p. injected with 10 μg of the compound, 100 μg of the compound per day, (100 μg of the compound and 1 μg 17β estradiol), so as to investigate anti-estrogens; and treated with 1 μg of 17β estradiol, wherein 50% DMSO/50% saline was used as injection media. These animals were sacrificed by $CO_2$ asphyxiation on Day 4. Their uteri were extracted, and excessive fats and all liquid were removed. Then the wet weight of the uteri was measured. A part of one corner of the uterus was separated and analyzed histologically. The rest part was used to isolate whole RNA, so as to evaluate the expression of complement component 3 gene.

| Table of the weight gain of uteri in some samples (n = 2): | |
|---|---|
| Samples | percentage of weight gain (%) |
| 2-[4-(dimethylamino-2-oxo-ethoxy)benzoyl]-3-(4-hydroxyphenyl)-6,7-dihydrogen-5H-furo[3,2-g]chromene | 26.2 |
| 2-[4-(diethylamino-2-oxo-ethoxy)benzoyl]-3-(4-hydroxyphenyl)-6,7-dihydrogen-5H-furo[3,2-g]chromene | 38.8 |
| 2-[4-(piperidine-2-oxo-ethoxy)benzoyl]-3-(4-hydroxyphenyl)-6,7-dihydrogen-5H-furo[3,2-g]chromene | 8.7 |
| 2-[4-(morpholine-2-oxo-ethoxy)benzoyl]-3-(4-hydroxyphenyl)-6,7-dihydrogen-5H-furo[3,2-g]chromene | 9.8 |
| 2-[4-(dimethylaminoethoxy)benzoyl]-3-(4-hydroxyphenyl)-6,7-dihydrogen-5H-furo[3,2-g]chromene | 0.6 |
| 2-[4-(diethylaminoethoxy)benzoyl]-3-(4-hydroxyphenyl)-6,7-dihydrogen-5H-furo[3,2-g]chromene | 12.2 |

Example 74

Procedure for Testing 6 Weeks Old Spayed Rats-Protection of Bone and Heart

One day after a Taconic Farm surgery, spayed or pseudo-spayed female Sprague-Dawley CD rats (weighted 240-275 g) were obtained. These animals were fed with food and sufficient water, 3 or 4 rats/cage, in a 12/12 (light/dark) cycle. After one day, all items of investigative treatments were started to these animals. The animals were administered 7 days/week following the instruction, continuously for 6 weeks. In each investigation, one group of rats that were not treated, comparably aged, and subjected to pseudo-surgeries was used as an untreated and estrogen-sufficient control group.

All treatments were conducted with specified concentrations in physiological saline solution containing 1% Tween 80, so that the amount of the treatment was 0.1 mL/100 g body weight. Then 17β estradiol was dissolved in corn oil (20 μg/mL), and administered subcutaneously to rats, 0.1 mL/rat. The result was measured according to the average body weight of each group, and the animals were dosed once every three weeks.

Five weeks after the beginning of the treatment and one week before the end of the treatment, the bone mineral density (BMD) of each rat was evaluated. The total densities and trabecular densities of the proximal ends of tibias in the anaesthetized rats were evaluated using XCT-960M (pQCT; Stratec Medizintechik, Pforzheim, Germany). The measuring procedure is shown as follows: 15 minutes before scanning, each rat was anaesthetized by intraperitoneal injection of 45 mg/kg ketamine, 8.5 mg/kg xylazine, and 1.5 mg/kg acepromazine.

The right hindlimb was drawn over the polycarbonate test tube with a diameter of 25 mm, and tied up on the acrylic acid scaffold, so that the anklebone was situated as a right angle and the knee joint was kept horizontally. The polycarbonate test tube was fixed on the sliding platform, so as to be orthogonal with the aperture of pQCTR. The platform was adjusted, so that the distal end of femur and the proximal end of tibia were within the scanning zone. The plane scan image was set as an image with a length of 10 mm and a linear resolution of 0.2 mm. When the scan image was displayed on the monitor, the proximal end of tibia was localized. pQCT scan was conducted from the point which was 3.4 mm away from the proximal end of tibia, with a thickness of 1 mm. The voxel (i.e. three-dimension pixel) had a size of 0.140 mm, and was composed of 145 slide projections.

After scanning, the image was displayed on the monitor, and showed the profile of the interesting zone including tibia but no fibula. Soft tissues were eliminated automatically using iterative algorithm. The density (total density) of the remaining bone was shown in a unit of $mg/cm^3$. In a concentric spiral separator, 55% of the external surface of the bone was peeled off. The density (i.e. trabecular density) of the remaining bone was shown in a unit of $mg/cm^3$. One week after BMD evaluation, the rats were sacrificed by $CO_2$ asphyxiation. Blood was collected so as to measure cholesterol. Uteri were extracted and weighted. Total cholesterol was measured by Boehringer-Mannheim Hitachi 911 clinic analyzer utilizing a cholesterol/HP kit. A statistical comparison was carried out by way of one-way ANOVA of Dunnet's test.

| Table of the weight gain of uteri in some samples (n = 2): | |
|---|---|
| Samples | percentage of weight gain (%) |
| 2-[4-(dimethylamino-2-oxo-ethoxy)benzoyl]-3-(4-hydroxyphenyl)-6,7-dihydrogen-5H-furo[3,2-g]chromene | 35.5 |
| 2-[4-(diethylamino-2-oxo-ethoxy)benzoyl]-3-(4-hydroxyphenyl)-6,7-dihydrogen-5H-furo[3,2-g]chromene | 23.9 |
| 2-[4-(piperidine-2-oxo-ethoxy)benzoyl]-3-(4-hydroxyphenyl)-6,7-dihydrogen-5H-furo[3,2-g]chromene | 12.4 |
| 2-[4-(morpholine-2-oxo-ethoxy)benzoyl]-3-(4-hydroxyphenyl)-6,7-dihydrogen-5H-furo[3,2-g]chromene | 6.2 |
| 2-[4-(dimethylaminoethoxy)benzoyl]-3-(4-hydroxyphenyl)-6,7-dihydrogen-5H-furo[3,2-g]chromene | 3.2 |
| 2-[4-(diethylaminoethoxy)benzoyl]-3-(4-hydroxyphenyl)-6,7-dihydrogen-5H-furo[3,2-g]chromene | 15.1 |

Example 75

Procedure of MCF-7/ERE Anti-Proliferation Assay

Stock solutions (usually, 0.1 M) of the test compounds were prepared in DMSO, and then diluted by 10-100 folds in DMSO, so as to achieve the working solutions with a concentration of 1-10 mM. The stock solutions (in DMSO) were stored at 4° C. (0.1 M) or −20° C. (<0.1 M). MCF-7 cells were passaged twice per week using a growth medium (i.e. a D-MEM/F-12 medium). The cells were kept in a 37° C., aerated flask in an incubator filled with 5% $CO_2$/95% humid air. One day before the treatment, a 96-well titration plate was coated with the cells in the medium, 25000 cells/well, and then cultured at 37° C., overnight.

The cells were transfected with 50 μL/well of ⅒ diluted adenovirus 5-ERE-tk-luciferase in the test medium (i.e. a D-MEM/F-12 medium without phenolsulfonphthalein) for 2 h. Then each well was washed once with 150μλ of the test medium. At last, the cells were divided into several replicates and treated at 37° C. for 24 h, wherein 8 wells were treated with 150μλ/well vehicle (≤0.1% v/v DMSO) or the compound diluted by ≥1000 folds with the test medium.

A primary screen of the test compounds was conducted with a single dose of 1 μM, wherein the test compound was alone (an agonist mode) or in combination with 0.1 nM 17β estradiol (EC80: an antagonist mode). Each 96-well plate also contained a vehicle control group (0.1% v/v DMSO) and an agonist control group (0.1 or 1 nM 17β estradiol). In the agonist and/or antagonist mode, a dose-response experiment was conducted for the active compounds which were increased by logarithm of $10^{-14} \sim 10^{-5}$ M. Based on these dose-response curves, $EC_{50}$ and $IC_{50}$ values were determined respectively. The final titration wells in each treatment groups contained 5 μL of $3 \times 10^{-5}$ M ICC-182780 ($10^{-6}$ M final concentration), as an ER antagonist control.

After the treatment, the cells were lysed in 25 μL/well of 1× cell-culture lytic agent (Promega Corporation) for 15 min. Cell lysate (20 μL) was transferred into a 96-well photometer plate. The luciferase activity was measured with 100 μL/well of the substrate for luciferase (Promega Corporation) in MicroLumat LB 96P photometer (EG&G Berthold). Before adding the substrate, a background measurement was performed for each well for 1 s. After adding the substrate, the luciferase activity was measured after 1 s delay and within 10 s. The data obtained from the photometer were analyzed by JMF software (SAS Institute). Using this program, the background reading of the luciferase activity in each well was subtracted, and then the average and standard deviation were calculated for each group of treatment.

The above luciferase data were subjected to a logarithmic transformation, and the weights of the transformed results which were far away from the median was reduced using Huber M-estimator. The transformed and weighted data were analyzed using JMF software, so as to conduct a one-way ANOVA (D test). The results of the compound treatment groups were compared with that of a vehicle control group in the agonist mode, or with that of a positive agonist control group in the antagonist mode (0.1 nM 17β-estradiol). In terms of the initial single-dosage experiment, if the results of the compound treatment groups were significantly different from those of the corresponding control groups ($p<0.05$), then the results were expressed as a percentage of the 17β-estradiol control group. In addition, $EC_{50}$ and/or $IC_{50}$ values were determined from a nonlinear dose-response curve using JMF software.

Table of MCF-7 anti-proliferation assay for some samples (n = 2):

| Samples | $IC_{50}$ (μM) |
|---|---|
| 2-[4-(dimethylamino-2-oxo-ethoxy)benzoyl]-3-(4-hydroxyphenyl)-6,7-dihydrogen-5H-furo[3,2-g]chromene | 21.8 |
| 2-[4-(diethylamino-2-oxo-ethoxy)benzoyl]-3-(4-hydroxyphenyl)-6,7-dihydrogen-5H-furo[3,2-g]chromene | 42.3 |
| 2-[4-(piperidine-2-oxo-ethoxy)benzoyl]-3-(4-hydroxyphenyl)-6,7-dihydrogen-5H-furo[3,2-g]chromene | 5.6 |
| 2-[4-(morpholine-2-oxo-ethoxy)benzoyl]-3-(4-hydroxyphenyl)-6,7-dihydrogen-5H-furo[3,2-g]chromene | 4.9 |
| 2-[4-(dimethylaminoethoxy)benzoyl]-3-(4-hydroxyphenyl)-6,7-dihydrogen-5H-furo[3,2-g]chromene | 22.9 |
| 2-[4-(diethylaminoethoxy)benzoyl]-3-(4-hydroxyphenyl)-6,7-dihydrogen-5H-furo[3,2-g]chromene | 13.5 |

Example 76

Inhibition of LDL Oxidation

Antioxidant Activity

Swine aortas were obtained from a slaughterhouse, washed, and then transferred into cold PBS. Epithelial cells were collected from the aortas. Particularly, in order to collect the epithelial cells, intercostal blood vessel of the aorta was knotted, and one end of the aorta was clamped with a forceps. Fresh 0.2% collagenase (Sigma Type I) which had been filtered for sterilization was placed into the blood vessel, and another end of the blood vessel was clamped with a forceps so as to form a closed system. The aortas were cultured at 37° C. for 15-20 min, then collagenase solution was collected and centrifuged for 5 min. The resultant precipitate was resuspended in 7 mL epithelial cell medium (i.e. a DMEM/Ham'S F12 medium without phenolsulfonphthalein but supplemented with carbon stripped FBS (5%)), then seeded in a 100 mm dish and cultured at 37° C., 5% $CO_2$. Twenty minutes later, the cells were rinsed with PBS, and a fresh medium was added. The above process was repeated for 24 hours. After about one week, the cells were confluent. Usually, these epithelial cells were fed twice per week, and seeded with a ratio of 1:7 after the action of trypsin during confluence. In the case that the compound (5 μM) to be evaluated existed, 12.5 μg/mL LDL cell-mediated oxidation was carried out at 37° C. for 4 hours. The result was expressed as the percentage of oxidation inhibition, which was determined by analyzing free aldehyde by the TBARS (Thiobarbituric acid reactive substances) method.

Table of LDL antioxidant activity in some samples (n = 2):

| Samples | Oxidation inhibition rate (%) |
|---|---|
| 2-[4-(dimethylamino-2-oxo-ethoxy)benzoyl]-3-(4-hydroxyphenyl)-6,7-dihydrogen-5H-furo[3,2-g]chromene | 44.9 |
| 2-[4-(diethylamino-2-oxo-ethoxy)benzoyl]-3-(4-hydroxyphenyl)-6,7-dihydrogen-5H-furo[3,2-g]chromene | 36.8 |
| 2-[4-(piperidine-2-oxo-ethoxy)benzoyl]-3-(4-hydroxyphenyl)-6,7-dihydrogen-5H-furo[3,2-g]chromene | 22.6 |
| 2-[4-(morpholine-2-oxo-ethoxy)benzoyl]-3-(4-hydroxyphenyl)-6,7-dihydrogen-5H-furo[3,2-g]chromene | 12.4 |
| 2-[4-(dimethylaminoethoxy)benzoyl]-3-(4-hydroxyphenyl)-6,7-dihydrogen-5H-furo[3,2-g]chromene | 6.8 |
| 2-[4-(diethylaminoethoxy)benzoyl]-3-(4-hydroxyphenyl)-6,7-dihydrogen-5H-furo[3,2-g]chromene | 5.1 |

Example 77

Effect on the Proliferation of Breast Cancer Cells

Using standard pharmacological experimental methods easily found in reference documents, the capabilities of the inventive compounds to treat and inhibit different types of malignant tumors or over-proliferation diseases can be evaluated.

Spayed athymic nu/nu (nude) mice were used. One day before the injection of tumor cells, a release-controlled pill containing 0.36-1.7 mg of β estradiol (60- or 90-day release) or a placebo was implanted into the animal. The pill was introduced into the endo-sculpture zone subcutaneously using a 10-scaled precise rotor. Next, $1 \times 10^7$ MCF-7 cells or $1 \times 10^7$ BG-1 cells were injected into breast tissues of the mice subcutaneously. The cells were mixed with matrigel with a same volume, and the latter was a liquid preparation of basilar membrane substrate, so as to facilitate tumor construction. One day after the implantation of the tumor cells (i.e. an inhibition protocol), or after the tumor had reached a certain volume (i.e. a treatment protocol), the tested compounds could be evaluated through administration. The saline containing the compound in a 1% Tween-80 vehicle was administered intraperitoneally or orally every day. The volumes of the tumors were evaluated every 3 or 7 days.

Table of the activities of some samples (n = 2):

| Samples | $IC_{50}$ (μM) |
|---|---|
| 2-[4-(dimethylamino-2-oxo-ethoxy)benzoyl]-3-(4-hydroxyphenyl)-6,7-dihydrogen-5H-furo[3,2-g]chromene | 5.6 |
| 2-[4-(diethylamino-2-oxo-ethoxy)benzoyl]-3-(4-hydroxyphenyl)-6,7-dihydrogen-5H-furo[3,2-g]chromene | 25.2 |
| 2-[4-(piperidine-2-oxo-ethoxy)benzoyl]-3-(4-hydroxyphenyl)-6,7-dihydrogen-5H-furo[3,2-g]chromene | 11.5 |
| 2-[4-(morpholine-2-oxo-ethoxy)benzoyl]-3-(4-hydroxyphenyl)-6,7-dihydrogen-5H-furo[3,2-g]chromene | 46.7 |
| 2-[4-(dimethylaminoethoxy)benzoyl]-3-(4-hydroxyphenyl)-6,7-dihydrogen-5H-furo[3,2-g]chromene | 4.6 |
| 2-[4-(diethylaminoethoxy)benzoyl]-3-(4-hydroxyphenyl)-6,7-dihydrogen-5H-furo[3,2-g]chromene | 22.1 |

Example 78

Effect on the Generation of IL-6 and GM-CSF in HOB Cells

Human osteoclasts (HOBs) were plated onto a 96-well dish, in a density of $7\times10^3$ cells/well in a conventional HOB medium (a Ham's F12 supplemented with 28 mM HEPES, pH 7.4, 10% FCS, 1.1 mM $CaCl_2$, 2 mM glutamine and 1% antibiotic-antifungal agent). The next day, the cells were treated with the compound or vehicle (0.2% DMSO) for 30 min, and then IL-1β (1 ng/mL) and TNF-α (10 ng/mL) were added. The cultivation lasted for 18~24 hours. The levels of IL-6 and GM-CSF were measured using a commercially available ELISA kit. The compounds of the invention showed an inhibition of IL-6 and GM-CSF.

Table of the activities of some samples (n = 2):

| Samples | $IC_{50}$ (μM) |
|---|---|
| 2-[4-(dimethylamino-2-oxo-ethoxy)benzoyl]-3-(4-hydroxyphenyl)-6,7-dihydrogen-5H-furo[3,2-g]chromene | 25.8 |
| 2-[4-(diethylamino-2-oxo-ethoxy)benzoyl]-3-(4-hydroxyphenyl)-6,7-dihydrogen-5H-furo[3,2-g]chromene | 5.2 |
| 2-[4-(piperidine-2-oxo-ethoxy)benzoyl]-3-(4-hydroxyphenyl)-6,7-dihydrogen-5H-furo[3,2-g]chromene | 44.5 |
| 2-[4-(morpholine-2-oxo-ethoxy)benzoyl]-3-(4-hydroxyphenyl)-6,7-dihydrogen-5H-furo[3,2-g]chromene | 32.7 |
| 2-[4-(dimethylaminoethoxy)benzoyl]-3-(4-hydroxyphenyl)-6,7-dihydrogen-5H-furo[3,2-g]chromene | 3.6 |
| 2-[4-(diethylaminoethoxy)benzoyl]-3-(4-hydroxyphenyl)-6,7-dihydrogen-5H-furo[3,2-g]chromene | 38.1 |

Example 79

Effect on the Proliferation of Prostate Cancer Cells

DU-145 prostate cancer cells were plated onto a 96-well dish, in a density of $2\times10^3$ cells/well in a MEM Eagles medium without phenol red. Such a medium comprises Earles' balanced salt, 1% antibiotic-antifungal agent, 2 mM glutamine, 0.1 mM nonessential amino acids, 1 mM sodium pyruvate and 10% carbon stripped FCS. The next day, the compound and vehicle (0.2% DMSO) were added, and the medium was refreshed every 48 hours. The cultivation was stopped 5 days later. Proliferation was analyzed using the above Cyquant kit.

Table of the activities of some samples (n = 2):

| Samples | $IC_{50}$ (μM) |
|---|---|
| 2-[4-(dimethylamino-2-oxo-ethoxy)benzoyl]-3-(4-hydroxyphenyl)-6,7-dihydrogen-5H-furo[3,2-g]chromene | 8.5 |
| 2-[4-(diethylamino-2-oxo-ethoxy)benzoyl]-3-(4-hydroxyphenyl)-6,7-dihydrogen-5H-furo[3,2-g]chromene | 35.2 |
| 2-[4-(piperidine-2-oxo-ethoxy)benzoyl]-3-(4-hydroxyphenyl)-6,7-dihydrogen-5H-furo[3,2-g]chromene | 14.5 |
| 2-[4-(morpholine-2-oxo-ethoxy)benzoyl]-3-(4-hydroxyphenyl)-6,7-dihydrogen-5H-furo[3,2-g]chromene | 23.7 |
| 2-[4-(dimethylaminoethoxy)benzoyl]-3-(4-hydroxyphenyl)-6,7-dihydrogen-5H-furo[3,2-g]chromene | 43.6 |
| 2-[4-(diethylaminoethoxy)benzoyl]-3-(4-hydroxyphenyl)-6,7-dihydrogen-5H-furo[3,2-g]chromene | 17.1 |

Example 80

Effect on the Proliferation of Ovarian Cancer Cells SKOV3

Cells in the logarithmic growth phase were digested with trypsin, added to a 96-well plate, in a density of $6\times10^3$ cells/well, and cultured in a 37° C., 5% $CO_2$ incubator. The next day, the plated was transferred to and kept in a 4° C. incubator for 1 h after the adherence of most cells, so as to achieve synchronized growth of the cells. The supernatant was sucked out, and a RPMI 1640 medium containing 10% fetal calf serum (FCS) was added, 200 μL/well. The cells were grouped according to the design of the experiment. The injectable solution of the compound prepared with sterile physiological saline was added to the 96 wells, 200 μL/well, so that the concentrate of the medicament in each well were 1 mg/mL, 2 mg/mL and 5 mg/mL, respectively. A concentration of 0 mg/mL was used as a negative control group. After subsequent cultivation for 24, 48, or 72 h, 20 μL MTT solution (with a concentration of 5 mg/mL) was added to each well, respectively. The plate was shaken gently, returned to the incubator and incubated for another 4 h. Then the supernatant was sucked out completely, and 200 μL of dimethyl sulfoxide was added to each well. The plate was shaken for 5-10 min on a shaker. The absorption (A=580) of each well at a wavelength of 580 nm was measured using a microplate reader. The A=580 value was proportional to the number of live cells.

Table of the activities of some samples (n = 3):

| Samples | $IC_{50}$ (μM) |
|---|---|
| 2-benzoyl-3-(4-hydroxyphenyl)-6,7-dihydrogen-5H-furo[3,2-g]chromene | 0.8 |
| 2-benzoyl-3-[4-(diethylaminoethoxy)phenyl]-6,7-dihydrogen-5H-furo[3,2-g]chromene | 28.2 |
| 2-(4-chlorobenzoyl)-3-[4-(piperidinoethoxy)phenyl]-6,7-dihydrogen-5H-furo[3,2-g]chromene | 72.2 |
| 2-(4-chlorobenzoyl)-3-[4-(diethylaminoethoxy)phenyl]- | 8.5 |

Table of the activities of some samples (n = 3):

| Samples | IC$_{50}$ (μM) |
|---|---|
| 6,7-dihydrogen-5H-furo[3,2-g]chromene | |
| 2-(4-methylbenzoyl)-3-[4-(diethylaminoethoxy)phenyl]-6,7-dihydrogen-5H-furo[3,2-g]chromene | 29.7 |
| 2-(4-methylbenzoyl)-3-[4-(dimethylaminoethoxy)phenyl]-6,7-dihydrogen-5H-furo[3,2-g]chromene | 10.3 |
| 2-(4-bromobenzoyl)-3-[4-(morpholinoethoxy)phenyl]-6,7-dihydrogen-5H-furo[3,2-g]chromene | 42.5 |
| 2-(4-bromobenzoyl)-3-[4-(piperidinoethoxy)phenyl]-6,7-dihydrogen-5H-furo[3,2-g]chromene | 32.8 |
| -(4-bromobenzoyl)-3-[4-(dimethylaminoethoxy)phenyl]-6,7-dihydrogen-5H-furo[3,2-g]chromene | 19.0 |
| 2-[4-(piperidinoethoxy)benzoyl]-3-(4-methoxyphenyl)-6,7-dihydrogen-5H-furo[3,2-g]chromene | 14.5 |
| 2-[4-(diethylamino-ethoxy)benzoyl]-3-(4-methoxyphenyl)-6,7-dihydrogen-5H-furo[3,2-g]chromene | 14.5 |
| 2-[4-(piperidinoethoxy)benzoyl]-3-(4-hydroxyphenyl)-6,7-dihydrogen-5H-furo[3,2-g]chromene | 13.6 |
| 2-[4-(diethylaminoethoxy)benzoyl]-3-(4-hydroxyphenyl)-6,7-dihydrogen-5H-furo[3,2-g]chromene | 17.9 |

Example 81

Effect on the Proliferation of Osteosarcoma Cells U2OS-EGFP-4A12G

Cells in the logarithmic growth phase were digested with trypsin, counted with trypan blue, and prepared into a cellular suspension with a density of 1×10$^4$ cells/mL. The suspension was seeded in a 96-well plate, 200 μL/well, about 2×10$^3$ cells/well, and pre-cultured for 24 h. The injectable solution of the compound prepared with sterile physiological saline was added to the 96 wells, 200 μL/well, so that the concentrate of the medicament in each well was 1 mg/mL, 2 mg/mL or 5 mg/mL, respectively. A concentration of 0 mg/mL was used as a negative control group. After subsequent cultivation for 0 h, 12 h, 24 h or 48 h, 20 μL MTT solution (5 mg/mL) was added to each well. The cultivation was terminated after another 4 h incubation. The supernatant in each well was sucked out carefully, and 150 μL of dimethyl sulfoxide (DMSO) was added to each well. The plate was shaken for 10 min, so that formazan was dissolved thoroughly. The absorption value (A value) of each well was measured using an enzyme linked immunosorbent detector, at a selected wavelength of 490 nm. The measurement was repeated for 5 times.

Table of the activities of some samples (n = 3):

| Samples | IC$_{50}$ (μM) |
|---|---|
| 2-benzoyl-3-(4-hydroxyphenyl)-6,7-dihydrogen-5H-furo[3,2-g]chromene | 13.7 |
| 2-benzoyl-3-[4-(diethylaminoethoxy)phenyl]-6,7-dihydrogen-5H-furo[3,2-g]chromene | 16.5 |
| 2-(4-chlorobenzoyl)-3-(4-methoxyphenyl)-6,7-dihydrogen-5H-furo[3,2-g]chromene | 21.7 |
| 2-(4-chlorobenzoyl)-3-[4-(piperidinoethoxy)phenyl]-6,7-dihydrogen-5H-furo[3,2-g]chromene | 26.3 |
| 2-(4-chlorobenzoyl)-3-[4-(diethylaminoethoxy)phenyl]-6,7-dihydrogen-5H-furo[3,2-g]chromene | 36.1 |
| 2-(4-methylbenzoyl)-3-[4-(diethylaminoethoxy)phenyl]-6,7-dihydrogen-5H-furo[3,2-g]chromene | 5.8 |
| 2-(4-methylbenzoyl)-3-[4-(dimethylaminoethoxy)phenyl]-6,7-dihydrogen-5H-furo[3,2-g]chromene | 7.7 |
| 2-(4-bromobenzoyl)-3-[4-(morpholinoethoxy)phenyl]- | 5.0 |

Table of the activities of some samples (n = 3):

| Samples | IC$_{50}$ (μM) |
|---|---|
| 6,7-dihydrogen-5H-furo[3,2-g]chromene | |
| 2-(4-bromobenzoyl)-3-[4-(piperidinoethoxy)phenyl]-6,7-dihydrogen-5H-furo[3,2-g]chromene | 13.3 |
| -(4-bromobenzoyl)-3-[4-(dimethylaminoethoxy)phenyl]-6,7-dihydrogen-5H-furo[3,2-g]chromene | 15.6 |
| 2-[4-(piperidinoethoxy)benzoyl]-3-(4-methoxyphenyl)-6,7-dihydrogen-5H-furo[3,2-g]chromene | 5.1 |
| 2-[4-(diethylamino-ethoxy)benzoyl]-3-(4-methoxyphenyl)-6,7-dihydrogen-5H-furo[3,2-g]chromene | 5.5 |
| 2-[4-(piperidinoethoxy)benzoyl]-3-(4-hydroxyphenyl)-6,7-dihydrogen-5H-furo[3,2-g]chromene | 10.8 |
| 2-[4-(diethylaminoethoxy)benzoyl]-3-(4-hydroxyphenyl)-6,7-dihydrogen-5H-furo[3,2-g]chromene | 14.9 |

The invention claimed is:

1. A compound represented by formula I, a stereoisomer or a pharmaceutically acceptable salt thereof:

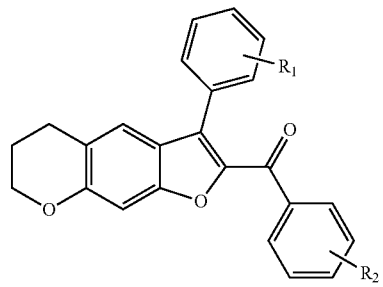

(I)

wherein
  $R_1$ can be optionally 1, 2 or 3 groups independently selected from H, halogen, —OH, —OCH$_3$, —CH$_3$, —NO$_2$, —O(CH$_2$)$_{n_1}$NR$_3$R$_4$, —O(CH$_2$)$_{n_2}$CONR$_5$R$_6$;
  $R_2$ can be optionally 1, 2 or 3 groups independently selected from H, halogen, —OH, —OCH$_3$, —CH$_3$, —NO$_2$, —O(CH$_2$)$_{n_1}$NR$_3$R$_4$, —O(CH$_2$)$_{n_2}$CONR$_5$R$_6$;
  wherein R$_3$R$_4$ is independently selected from methyl or ethyl, or R$_3$R$_4$, together with the nitrogen atom to which they are attached, form a pyrrolidinyl, methylpyrrolidinyl, dimethylpyrrolidinyl, piperidyl, morpholinyl, or hexamethylene imine ring;
  $n_1$ is an integer from 2 to 4;
  R$_5$R$_6$ is independently selected from methyl or ethyl, or R$_5$R$_6$, together with the nitrogen atom to which they are attached, form a pyrrolidinyl, methylpyrrolidinyl, dimethylpyrrolidinyl, piperidyl, morpholinyl, or hexamethylene imine ring; or is independently selected from hydrogen and a phenyl group; and
  $n_2$ is an integer from 1 to 3.

2. A pharmaceutical composition, comprising a compound of claim 1, as an active component; and a pharmaceutically acceptable carrier or diluent.

3. A method for treating breast cancer, prostate cancer, ovary cancer or osteosarcoma comprising administering to a subject in need thereof a therapeutically effective amount of the compound of claim 1.

4. The compound of claim 1 being:
  2-[4-(dimethylamino-2-oxo-ethoxy)benzoyl]-3-(4-hydroxyphenyl)-6,7-dihydrogen-5H-furo[3,2-g]chromene;

2-[4-(diethylamino-2-oxo-ethoxy)benzoyl]-3-(4-hydroxyphenyl)-6,7-dihydrogen-5H-furo[3,2-g]chromene;
2-[4-(piperidine-2-oxo-ethoxy)benzoyl]-3-(4-hydroxyphenyl)-6,7-dihydrogen-5H-furo[3,2-g]chromene;
2-[4-(morpholine-2-oxo-ethoxy)benzoyl]-3-(4-hydroxyphenyl)-6,7-dihydrogen-5H-furo[3,2-g]chromene;
2-[4-(dimethylaminoethoxy)benzoyl]-3-(4-hydroxyphenyl)-6,7-dihydrogen-5H-furo[3,2-g]chromene; or
2-[4-(diethylaminoethoxy)benzoyl]-3-(4-hydroxyphenyl)-6,7-dihydrogen-5H-furo[3,2-g]chromene.

* * * * *